United States Patent

Misaki et al.

(10) Patent No.: US 6,706,732 B1
(45) Date of Patent: *Mar. 16, 2004

(54) NASAL PREPARATION OF GUANIDINOIMINO QUINOLINE DERIVATIVES

(75) Inventors: Masafumi Misaki, Takarazuka (JP); Shigeyuki Takada, Nishinomiya (JP); Mitsuru Shiraishi, Amagasaki (JP); Shoji Fukumoto, Kobe (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/980,391

(22) PCT Filed: Jun. 1, 2000

(86) PCT No.: PCT/JP00/03559

§ 371 (c)(1),
(2), (4) Date: Nov. 28, 2001

(87) PCT Pub. No.: WO00/75115

PCT Pub. Date: Dec. 14, 2000

(30) Foreign Application Priority Data

Jun. 3, 1999 (JP) .............................. 11-156773

(51) Int. Cl.[7] ........................ A61K 31/47; C07D 215/40
(52) U.S. Cl. ........................ 514/311; 546/171
(58) Field of Search ............................ 546/171; 514/311

(56) References Cited

U.S. PATENT DOCUMENTS

| | | | |
|---|---|---|---|
| 5,395,855 A | 3/1995 | Stanek et al. | |
| 5,591,754 A | 1/1997 | Lang et al. | 514/331 |
| 5,700,839 A | 12/1997 | Gericke et al. | 514/618 |
| 5,783,576 A | 7/1998 | Bechtel et al. | 514/242 |
| 6,093,729 A | 7/2000 | Schwark et al. | |
| 6,350,749 B1 * | 2/2002 | Shiraishi et al. | 514/248 |

FOREIGN PATENT DOCUMENTS

| | | |
|---|---|---|
| EP | 0 681 833 A2 | 11/1995 |
| EP | 0 708 091 A1 | 4/1996 |
| EP | 0825187 | 2/1998 |
| EP | 0 950 418 A2 | 10/1999 |
| EP | 1 057 812 A1 | 12/2000 |
| JP | 60-239454 | 11/1985 |
| JP | 6-509798 | 11/1994 |
| JP | 9-505035 | 5/1997 |
| JP | 9-291026 | 11/1997 |
| JP | 10-114744 | 5/1998 |
| WO | WO 96/04241 | 2/1996 |
| WO | WO 98/19682 | 5/1998 |

* cited by examiner

*Primary Examiner*—Rita Desai
(74) *Attorney, Agent, or Firm*—Mark Chao; Elaine M. Ramesh

(57) ABSTRACT

A nasal preparation comprising a compound represented by the formula:

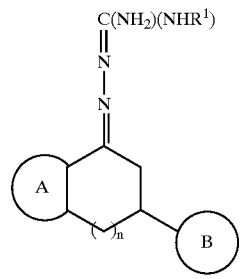

wherein Ring A is an optionally substituted 5- or 6-membered aromatic heterocyclic ring, Ring B is an optionally substituted 5- or 6-membered aromatic homocyclic or heterocyclic ring, $R^1$ is a hydrogen atom, a hydroxyl group or a lower alkyl group, and n is 0 or 1, which has an Na—H exchange inhibiting activity, or a salt thereof exhibits excellent bioabsorbability and an Na—H exchange inhibiting activity superior to that of an oral preparation, thus being useful as a prophylactic and/or therapeutic agent for ischemic heart diseases such as myocardial infarct and arrhythmia.

4 Claims, 2 Drawing Sheets

NASAL PREPARATION OF GUANIDINOIMINO QUINOLINE DERIVATIVES

This application is the National Stage of International Application No. PCT/JP00/03559, filed on Jun. 1, 2000.

FIELD OF THE INVENTION

The present invention relates to a nasal preparation which contains a novel aminoguanidine hydrazone derivative and the like. A nasal preparation according to the present invention has a prophylactic and therapeutic effect on myocardial infarction and accompanying dysfunctions, arrhythmia, unstable angina, cardiac hypertrophy, restenosis after PTCA (percutaneous transluminal coronary angioplasty), hypertension and accompanying tissue failures and the like, since its active ingredient, i.e., amino guanidine hydrazone derivative, has a sodium-proton (Na—H) exchange inhibiting activity.

BACKGROUND OF THE INVENTION

While various pharmaceuticals were developed and employed in clinical practice widely, most of them are employed as oral or injectable preparations. An injectable preparation is employed instead of an oral preparation, when an active ingredient is poorly absorbed orally due to an instability in a digestive tract, a poor migration through the wall of a digestive tract and a disadvantageous first pass effect, or when an active ingredient has a digestive tract tissue damaging effect, or when a pharmacological effect should be exerted instantaneously. However, administration via an injection poses a substantial pain to a patient and a substantial inconvenience due to the impossibility of being performed by a patient himself, and becomes problematic especially when the treatment is prolonged.

A nasal administration is an attractive non-injection method for administering an agent conveniently. A nasal administration is advantageous because it can be performed by a patient himself and also because it is scarcely subjected to a metabolism in a liver (first-pass effect) due to a direct introduction of an agent into a systemic blood circulation, and also advantageous because it may exhibit a rapid pharmacological effect due to a generally rapid absorption of an agent once given nasally.

On the other hand, an Na—H exchange inhibitor which is considered to have an improving effect or a cell protecting effect on a cytopathy under an ischemic condition (especially on a myocardial cell) is an attractive agent in the field of the treatment of ischemic diseases.

Various acylguanidine derivatives are disclosed as Na—H exchange inhibitors in JP-A-6-228082, WO96/04241, EP708091 and EP708088.

JP-A-6-509798 discloses a pyrazine derivative represented by the formula:

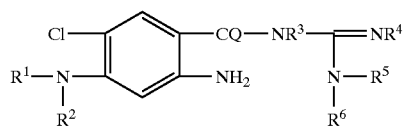

wherein $R^1$ is H or a $C_{1-6}$ alkyl, $R^2$ is 1-morpholinyl, an optionally substituted $C_{1-6}$ alkyl and the like, $R^3$, $R^4$, $R^5$ and $R^4$ are same or different and each denotes hydrogen, a $C_{1-6}$ alkyl or benzyl as an agent which has an Na—H exchange inhibiting effect and which may be administered as a nasal preparation.

JP-A-9-504535 discloses a benzoylguanidine derivative represented by the formula:

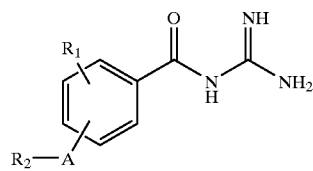

wherein A is $—C_mH_{2m}—NR_4—$ and the like, $R^1$ is F, Cl, $CF_3$, $R^1—SO_2—$ or $R^1—NH—SO_2—$ (in which $R^1$ is a $C_{1-5}$ alkyl, halogen- or phenyl-substituted $C_{1-5}$ alkyl and the like), $R_2$ is a group represented by the formula:

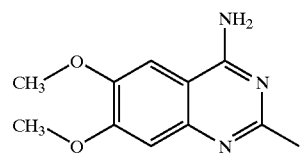

and $R_3$, $R_4$ and $R_5$ are same or different and each denotes hydrogen or a $C_{1-4}$ alkyl and the like as an agent which has an Na—H exchange inhibiting effect and which may be administered as nose drops if possible.

JP-A-9-505035 discloses a pyrazine carboxyamide derivative represented by the formula:

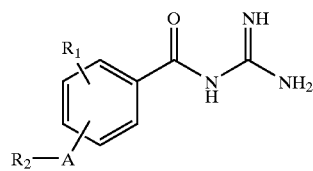

wherein A is $—C_mH_{2m}—NR_4—$ and the like which is bound via a nitrogen atom to a pyrazine carboxyamide system, $R_1$ is hydrogen, fluorine, chlorine, a $C_{1-4}$ alkyl and the like, $R_2$ is a group represented by the formula:

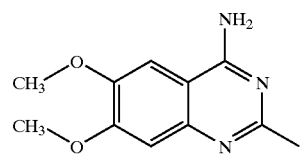

and $R_3$, $R_4$ and $R_4'$ are same or different and each denotes hydrogen or a $C_{1-4}$ alkyl and the like as an agent which has an Na—H exchange inhibiting effect and which may be administered as nose drops if possible.-

WO98/19682 discloses an aminosterol compound represented by the formula:

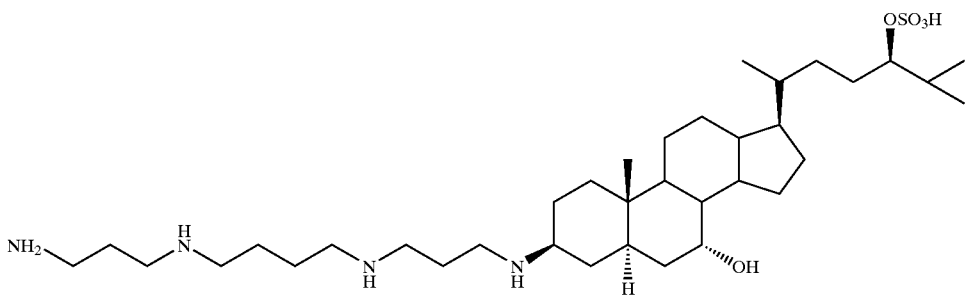

as an agent which has an Na—H exchange inhibiting effect and which can be administered to a nasal cavity.

SUMMARY OF THE INVENTION

An objective of the present invention is to provide a nasal preparation which exerts an excellent effect as a prophylactic and therapeutic agent for myocardial infarction and accompanying dysfunctions, arrhythmia, unstable angina, cardiac hypertrophy, restenosis after PTCA, hypertension and accompanying tissue failures and the like and is a sufficiently satisfactory pharmaceutical composition when compared with an oral preparation or an injectable preparation.

The present inventors have studied nasal preparations intensively for obtaining a prophylactic and therapeutic agent described above. As a result, it has been found that a novel aminoguanidine hydrazone compound represented by the formula (I):

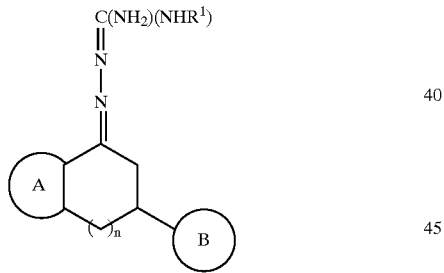

wherein Ring A is an optionally substituted 5- or 6-membered aromatic heterocyclic ring, Ring B is an optionally substituted 5- or 6-membered aromatic homocyclic or heterocyclic ring, $R^1$ is a hydrogen atom, a hydroxyl group or a lower alkyl group, and n is 0 or 1, or a salt thereof (hereinafter abbreviated as Compound (I)) exhibits an excellent Na—H exchange inhibiting activity (especially NHE-1 selective Na—H exchange inhibiting activity) as well as an excellent in vivo absorption via a nasal mucosa and an excellent migration into a heart, and exerts an unexpectedly excellent pharmacological activity, when used in a nasal preparation, which is comparable with an oral or injectable preparation and is satisfactory characteristically as a medicine, whereby establishing the present invention.

Thus, the present invention relates to:

(1) a nasal preparation comprising a compound represented by the formula (I) or a prodrug thereof;

(2) the nasal preparation as described in the above (1), wherein Ring A is a 5- or 6-membered nitrogen-containing aromatic heterocyclic ring containing 1 or 2 nitrogen atoms optionally substituted by an optionally halogenated $C_{1-6}$ alkyl or an optionally halogenated $C_{1-6}$ alkoxy, Ring B is a 5- or 6-membered aromatic homocyclic or heterocyclic ring optionally containing one heteroatom selected from the group consisting of oxygen, sulfur and nitrogen atoms which is optionally substituted by a halogen atom, an optionally halogenated $C_{1-6}$ alkyl, a hydroxyl group or an optionally halogenated $C_{1-6}$ alkoxy, $R^1$ is a hydrogen atom or a hydroxyl group, and n is 1;

(3) the nasal preparation as described in the above (1) comprising (±)-7-(2-chlorophenyl)-5-guanidinoimino-4-methyl-5,6,7,8-tetrahydroquinoline or a prodrug or a salt thereof; (±)-7-(5-fluoro-2-methylphenyl)-5-guanidinoimino-4-methyl-5,6,7,8-tetrahydroquinoline or a prodrug or a salt thereof; or (±)-7-(2-chloro-5-fluorophenyl)-5-guanidinoimino-4-methyl-5,6,7,8-tetrahydroquinoline or a prodrug or a salt thereof;

(4) the nasal preparation as described in the above (1) comprising (S)-(-)-(2-chlorophenyl)-5-guanidinoimino-4-methyl-5,6,7,8-tetrahydroquinoline or a prodrug or a salt thereof; (S)-(-)-7-(5-fluoro-2-methylphenyl)-5-guanidinoimino-4-methyl-5,6,7,8-tetrahydroquinoline or a prodrug or a salt thereof; or (S)-(-)-7-(2-chloro-5-fluorophenyl)-5-guanidinoimino-4-methyl-5,6,7,8-tetrahydroquinoline or a prodrug or a salt thereof;

(5) the nasal preparation as described in the above (1) which is a prophylactic and therapeutic agent for an ischemic heart disease;

(6) the nasal preparation as described in the above (1), wherein said ischemic heart disease is myocardial infarction, unstable angina or arrhythmia;

(7) the nasal preparation as described in the above (1) which is a prophylactic and therapeutic agent for cardiac insufficiency;

(8) (S)-(-)-7-(5-Fluoro-2-methylphenyl)-5-guanidinoimino-4-methyl-5,6,7,8-tetrahydroquinoline or a prodrug or a salt thereof;

(9) (S)-(-)-7-(2-Chloro-5-fluorophenyl)-5-guanidinoimino-4-methyl-5,6,7,8-tetrahydroquinoline or a prodrug or a salt thereof;

(10) a pharmaceutical composition comprising (S)-(-)-7-(5-fluoro-2-methylphenyl)-5-guanidinoimino-4-methyl-5,6,7,8-tetrahydroquinoline or a prodrug or a salt thereof; or (S)-(-)-7-(2-chloro-5-fluorophenyl)-5-guanidinoimino-4-methyl-5,6,7,8-tetrahydroquinoline or a prodrug or a salt thereof;

(11) the composition as described in the above (10) which is an Na—H exchange inhibitor;

(12) the composition as described in the above (10) which is a nasal preparation;

(13) the composition as described in the above (10) which is a prophylactic and therapeutic agent for an ischemic heart disease;

(14) the composition as described in the above (13), wherein said ischemic heart disease is myocardial infarction, unstable angina or arrhythmia;

(15) the composition as described above in the above (10) which is a prophylactic and therapeutic agent for cardiac insufficiency;

(16) use of (S)-(-)-7-(5-fluoro-2-methylphenyl)-5-guanidinoimino-4-methyl-5,6,7,8-tetrahydroquinoline or a prodrug or a salt thereof; or (S)-(-)-7-(2-chloro-5-fluorophenyl)-5-guanidinoimino-4-methyl-5,6,7,8-tetrahydroquinoline or a prodrug or a salt thereof for manufacturing an Na—H exchange inhibitor; and,

(17) a method for inhibiting an Na—H exchange in mammals comprising administering an effective amount of (S)-(-)-7-(5-fluoro-2-methylphenyl)-5-guanidinoimino-4-methyl-5,6,7,8-tetrahydroquinoline or a prodrug or a salt thereof; or (S)-(-)-7-(2-chloro-5-fluorophenyl)-5-guanidinoimino-4-methyl-5,6,7,8-tetrahydroquinoline or a prodrug or a salt thereof to said mammals.

Figure 1:
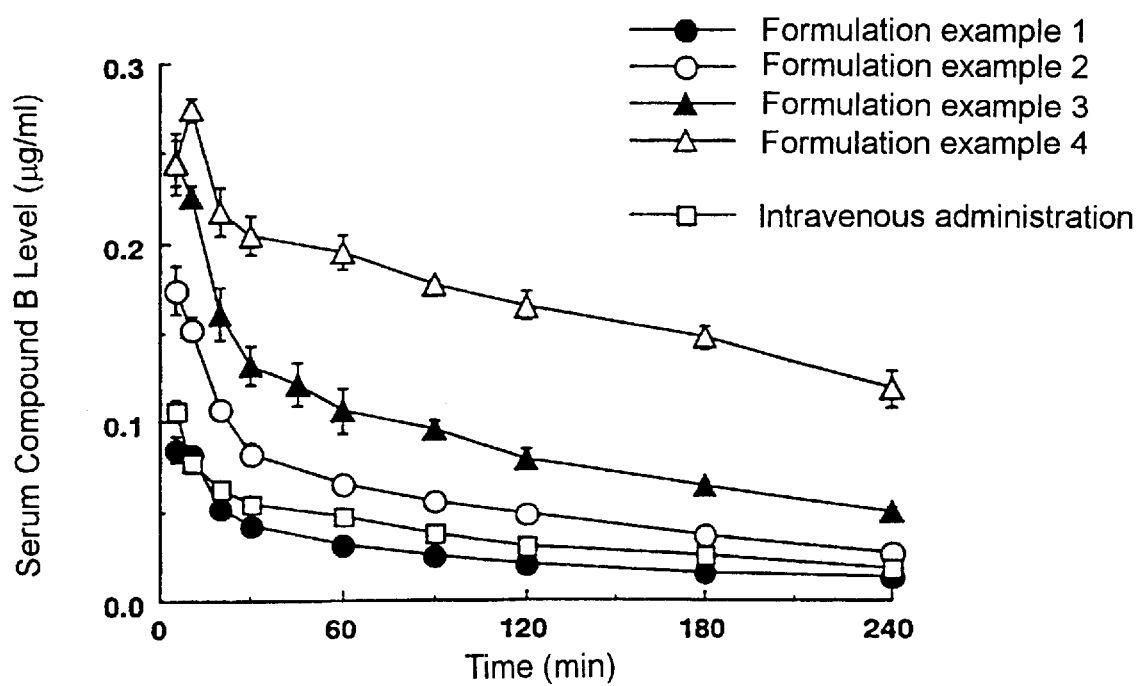
FIG. 1 shows the change in the serum level of Compound B after the nasal administration of Formulations 1 to 4 and after the intravenous administration of the formulation of Comparative 1.

In the above formula (I), Ring A denotes an optionally substituted 5- or 6-membered aromatic heterocyclic ring.

The aromatic heterocyclic ring in the "optionally substituted 5- or 6-membered aromatic heterocyclic ring" represented by A may for example be an aromatic heterocyclic ring having as an atom constituting the ring system (a ring atom) at least one (preferably 1 to 3, more preferably 1 or 2) atom of 1 to 3 (preferably 1 to 2) heteroatoms selected from the group consisting of oxygen, sulfur and nitrogen atoms.

The "aromatic heterocyclic ring" may for example be a 5- or 6-membered aromatic heterocyclic ring such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, pyridine, pyridazine, pyrimidine, pyrazine, triazine and the like.

Among those listed above, a 5- or 6-membered aromatic heterocyclic ring having 1 to 3 (preferably 1 to 2) heteroatoms selected from the group consisting of oxygen, sulfur and nitrogen atoms, and typical examples of Ring A are a pyridine ring, a pyridazine ring, a pyrrole ring, a pyrazole ring, a furan ring, a thiophene ring, an isoxazole ring, a pyrimidine ring (preferably a 5- or 6-membered nitrogen-containing aromatic heterocyclic ring containing 1 or 2 nitrogen atoms such as a pyridine ring, a pyridazine ring, a pyrrole ring, a pyrazole ring and the like, more preferably a 5- or 6-membered nitrogen-containing aromatic heterocyclic ring containing 1 or 2 nitrogen atoms such as a pyridine ring, a pyrazole ring, a pyridazine ring and the like), most preferably a pyridine ring and the like.

In the above formula (I), Ring B is an optionally substituted 5- or 6-membered aromatic homocyclic or heterocyclic ring.

The "optionally substituted 5- or 6-membered aromatic homocyclic ring" represented by B may for example be an optionally substituted benzene ring and the like.

The aromatic heterocyclic ring in the "optionally substituted 5- or 6-membered aromatic hetercyclic ring" represented by B may for example be an aromatic heterocyclic ring having as an atom constituting the ring system (a ring atom) at least one (preferably 1 to 3, more preferably 1 or 2) atom of 1 to 3 (preferably 1 to 2) heteroatoms selected from the group consisting of oxygen, sulfur and nitrogen atoms.

The "aromatic heterocyclic ring" may for example be a 5- or 6-membered aromatic heterocyclic ring such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, pyridine, pyridazine, pyrimidine, pyrazine, triazine and the like, with a 5- or 6-membered aromatic heterocyclic ring containing 1 to 3 (preferably 1 or 2) heteroatoms selected from the group consisting of oxygen, sulfur and nitrogen atoms.

Preferred Ring B may typically be a 5- or 6-membered aromatic homocyclic or heterocyclic ring which may contain one heteroatom selected from the group consisting of oxygen, sulfur and nitrogen atoms such as a benzene ring, a pyrrole ring, a furan ring, a thiophene ring, a pyridine ring (preferably a benzene ring, a furan ring, a thiophene ring and the like), most preferably a benzene ring and the like.

Ring A and Ring B may be substituted in any possible position which may be same or different by 1 to 4 (preferably 1 to 2) substituents selected from the group consisting of (1) a halogen atom, (2) a hydroxyl group, (3) a nitro group, (4) a cyano group, (5) an optionally substituted lower alkyl group, (6) an optionally substituted lower alkenyl group, (7) an optionally substituted lower alkynyl group, (8) an optionally substituted lower aralkyl group, (9) an optionally substituted lower alkoxy group, (10) an optionally substituted mercapto group, (11) an optionally substituted amino group, (12) an optionally esterified or amidated carboxyl group, (13) an optionally substituted sulfonyl group, (14) an optionally substituted acyl group and (15) an optionally substituted phenyl group, wherein (16) two adjacent substituents may be taken together to form a divalent hydrocarbon group, or the nitrogen atom in Ring A or Ring B may be oxidized.

When Ring A or Ring B is a nitrogen-containing aromatic heterocylcic ring having as a substituent a hydroxyl group such as a 2-oxypyridine ring then Ring A or Ring B may denote a nitrogen-containing aromatic heterocyclic ring having an oxo group (which is equivalent structurally to a nitrogen-containing aromatic heterocyclic ring having as a substituent a hydroxyl group) such as α-pyridone, and when Ring A or ring B is a nitrogen-containing aromatic heterocyclic ring having an oxo group then the substituent which may be possessed by Ring A or Ring B may be present on the nitrogen atom on Ring A or Ring B.

The halogen atom of (1) described above may for example be chlorine, bromine, fluorine, iodine and the like.

The optionally substituted lower alkyl group of (5) described above may for example be a $C_{1-6}$ alkyl group (for example, methyl, ethyl, propyl, isopropyl, butyl, isobutyl t-butyl, s-butyl, pentyl, hexyl and the like).

Such lower alkyl group may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The optionally substituted lower alkenyl group of (6) described above may for example be a $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

Such lower alkenyl group may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The optionally substituted lower alkynyl group of (7) described above may for example be a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

Such lower alkynyl group may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The optionally substituted lower aralkyl group of (8) described above may for example be a $C_{7-10}$ aralkyl group (preferably phenyl-$C_{1-6}$ alkyl group) such as benzyl, phenethyl and the like.

Such lower aralkyl group may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkyl group (for example, methyl, ethyl, propyl, isopropyl, butyl, isobutyl, s-butyl, t-butyl, pentyl, hexyl and the like), a halogeno-lower ($C_{1-6}$) alkyl group (for example, $CF_3$, $CF_2CF_3$, $CH_2F$, $CHF_2$ and the like), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The optionally substituted lower alkoxy group of (9) described above may for example be a $C_{1-6}$ alkoxy group (for example, methoxy, ethoxy, propoxy, isopropoxy, butoxy, s-butoxy, t-butoxy, pentyloxy, isopentyloxy, neopentyloxy, hexyloxy and the like).

Such lower alkoxy group may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The optionally substituted mercapto group of (10) described above may for example be an optionally substituted $C_{1-6}$ alkylthio group (for example, methylthio, ethylthio, propylthio, isopropylthio, butylthio, s-butylthio, t-butylthio, pentylthio, isopentylthio, neopentylthio, hexylthio and the like).

Such $C_{1-6}$ alkylthio group may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The optionally substituted amino group of (11) described above may for example be an amino acid which may optionally be substituted by 1 or 2 same or different substituents selected from the group consisting of a lower ($C_{1-6}$) alkyl group (for example, methyl, ethyl, propyl, isopropyl, butyl, isobutyl, s-butyl, t-butyl, pentyl, hexyl and the like), a lower ($C_{1-6}$) alkoxy group (for example, methoxy, ethoxy, propoxy, isopropoxy, butoxy, isobutoxy, s-butoxy, t-butoxy, pentyloxy, hexyloxy and the like), a halogeno-lower ($C_{1-6}$) alkyl group (for example, $CF_3$, $CF_2CF_3$, $CH_2F$, $CHF_2$ and the like), a lower ($C_{3-6}$) cycloalkyl (for example, cyclopropyl, cyclobutyl, cyclopentyl, cyclohexyl and the like), a hydroxyl group, carbamoyl, phenyl, a phenyl-lower ($C_{1-6}$) alkyl (for example, benzyl, phenethyl, 3-phenylpropyl, 4-phenylbutyl and the like), a lower ($C_{1-6}$) alkyl-carbonyl(alkanoyl) (for example, formyl, acetyl, propionyl, butyryl, isobutyryl, valeryl, pivaloyl and the like), a $C_{3-6}$ cycloalkyl-carbonyl (for example, cyclopropylcarbonyl, cyclobutylcarbonyl, cyclopentylcarbonyl, cyclohexylcarbonyl and the like), benzoyl, a phenyl-$C_{2-6}$ alkanoyl (for example, phenylacetyl, phenylpropionyl and the like), a lower ($C_{1-6}$) alkoxy-carbonyl (for example, methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl and the like), phenoxycarbonyl, a phenyl-lower ($C_{1-6}$) alkoxy-carbonyl (for example, benzyloxycarbonyl, phenylethoxycarbonyl and the like), a lower ($C_{1-6}$) alkylsulfinyl (for example, methylsulfinyl, ethylsulfinyl, propylsulfinyl, isopropylsulfinyl, butylsulfinyl, isobutylsulfinyl, s-butylsulfinyl, t-butylsulfinyl, pentylsulfinyl, hexylsulfinyl and the like), a $C_{3-6}$ cycloalkylsulfinyl (for example, cyclopropylsulfinyl, cyclobutylsulfinyl, cyclopentylsulfinyl, cyclohexylsulfinyl and the like), phenylsulfinyl, a lower ($C_{1-6}$) alkylsulfonyl (for example, methylsulfonyl, ethylsulfonyl, propylsulfonyl, isopropylsulfonyl, butylsulfonyl, isobutylsulfonyl, t-butylsulfonyl, s-butylsulfonyl, pentylsulfonyl, hexylsulfonyl and the like), a $C_{3-6}$ cycloalkylsulfonyl (for example, cyclopropylsulfonyl, cyclobutylsulfonyl, cyclopentylsulfonyl, cyclohexylsulfonyl and the like), a lower ($C_{1-6}$) alkoxysulfonyl (for example, methoxysulfonyl, ethoxysulfonyl, propoxysulfonyl, isopropoxysulfonyl, butoxysulfonyl, isobutoxysulfonyl, s-butoxtysulfonyl, t-butoxysulfonyl, pentyloxysulfonyl, hexyloxysulfonyl and the like) and phenylsulfonyl and the like.

It is also possible that two substituents listed above are taken together with a nitrogen atom to form a cyclic amino group, such as pyrrolidino, piperidino, morpholino, thiomorpholino and the like.

Each optionally substituted amino group exemplified above may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkyl group (for example, methyl, ethyl, propyl, isopropyl, butyl, isobutyl, s-butyl, t-butyl, pentyl, hexyl and the like), a halogeno-lower ($C_{1-6}$) alkyl group (for example, $CF_3$, $CF_2CF_3$, $CH_2F$, $CHF_2$ and the like), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The optionally esterified or amidated carboxyl group of (12) described above includes:

an esterified carboxy group such as a lower ($C_{1-6}$) alkoxy-carbonyl group (for example, methoxycarbonyl, ethoxycarbonyl, propoxycarbonyl, isopropoxycarbonyl, butoxycarbonyl, s-butoxycarbonyl, t-butoxycarbonyl, pentyloxycarbonyl, isopentyloxycarbonyl, neopentyloxycarbonyl, hexyloxycarbonyl and the like), a $C_{3-6}$ cycloalkoxy-carbonyl (for example, cyclopropoxycarbonyl, cyclobutyloxycarbonyl, cyclopentyloxycarbonyl, cyclohexyloxycarbonyl and the like), a phenyl-lower ($C_{1-6}$) alkoxy-carbonyl (for example, benzyloxycarbonyl, phenylethoxycarbonyl and the like), a nitroxy lower ($C_{1-6}$) alkoxy-carbonyl (for example, 2-nitroxyethoxycarbonyl, 3-nitroxypropoxycarbonyl and the like) and the like;

an amidated carboxyl group such as carbamoyl, N-mono-lower ($C_{1-6}$) alkyl-carbamoyl (for example, methylcarbamoyl, ethylcarbamoyl, propylcarbamoyl, isopropylcarbamoyl, butylcarbamoyl, isobutylcarbamoyl, s-butylcarbamoyl, t-butylcarbamoyl, pentylcarbamoyl, hexylcarbamoyl and the like), an N,N-di-lower ($C_{1-6}$) alkyl-carbamoyl (for example, N,N-dimethylcarbamoyl, N,N-diethylcarbamoyl, N,N-dipropylcarbamoyl, N,N-dibutylcarbamoyl and the like), a $C_{3-7}$ cycloalkyl-carbamoyl (for example, cyclopropylcarbamoyl, cyclobutylcarbamoyl, cyclopentylcarbamoyl, cyclohexylcarbamoyl and the like), a phenyl-lower ($C_{1-6}$) alkyl-carbamoyl (for example, benzylcarbamoyl, phenethylcarbamoyl and the like), a nitroxy lower ($C_{1-6}$) alkylamino-carbonyl (for example, 2-nitroxyethylcarbamoyl, 3-nitroxypropylcarbamoyl and the like), a cyclic aminocarbonyl (for example, morpholinocarbonyl, piperidinocarbonyl, pyrrolidinocarbonyl, thiomorpholinocarbonyl and the like), anilinocarbonyl and the like.

Each "optionally esterified or amidated carboxyl group" exemplified above may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkyl group (for example, methyl, ethyl, propyl, isopropyl, butyl, isobutyl, s-butyl, t-butyl, pentyl, hexyl and the like), a halogeno-lower ($C_{1-6}$) alkyl group (for example, $CF_3$, $CF_2CF_3$, $CH_2F$, $CHF_2$ and the like), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The optionally substituted sulfonyl group of (13) described above may for example be a lower ($C_{1-6}$) alkyl-sulfonyl (for example, a lower ($C_{1-6}$) alkylsulfonyl (for example, methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, hexylsulfonyl and the like), a $C_{3-6}$ cycloalkylsulfonyl (for example, cyclopropylsulfonyl, cyclobutylsulfonyl, cyclopentylsulfonyl, cyclohexylsulfonyl and the like), a phenyl-$C_{1-6}$ alkylsulfonyl (for example, benzylsulfonyl, phenethylsulfonyl and the like), a lower ($C_{1-6}$) alkoxysulfonyl (for example, methoxysulfonyl, ethoxysulfonyl, propoxysulfonyl, isopropoxysulfonyl, butoxysulfonyl, isobutoxysulfonyl, s-butoxysulfonyl, t-butoxysulfonyl, pentyloxysulfonyl, hexyloxysulfonyl and the like), a $C_{3-6}$ cycloalkyloxysulfonyl (for example, cyclopropoxysulfonyl, cyclobutyloxysulfonyl, cyclopentyloxysulfonyl, cyclohexyloxysulfonyl and the like), a phenyl-lower ($C_{1-6}$) alkoxysulfonyl (for example, benzyloxysulfonyl, phenethyloxysulfonyl and the like), sulfamoyl, a lower ($C_{1-6}$) alkylaminosulfonyl (for example, methylaminosulfonyl, ethylaminosulfonyl, propylaminosulfonyl, isopropylaminosulfonyl, butylaminosulfonyl, isobutylaminosulfonyl, s-butylaminosulfonyl, t-butylaminosulfonyl, pentylaminosulfonyl, hexylaminosulfonyl and the like), a $C_{3-6}$ cycloalkylaminosulfonyl (for example, cyclopropylaminosulfonyl, cyclobutylaminosulfonyl, cyclopentylaminosulfonyl, cyclohexylaminosulfonyl and the like), a phenyl-lower ($C_{1-6}$) alkylaminosulfonyl (for example, benzylaminosulfonyl, phenethylaminosulfonyl and the like), a cyclic aminosulfonyl (for example, morpholinosulfonyl, piperidinosulfonyl, pyrrolidinosulfonyl, thiomorpholinosulfonyl and the like), a nitroxy lower ($C_{1-6}$) alkylamino-sulfonyl (for example, 2-nitroxyethylaminosulfonyl, 3-nitroxypropylaminosulfonyl and the like), anilinosulfonyl and the like.

Each "optionally substituted sulfonyl group" exemplified above may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkyl group (for example, methyl, ethyl, propyl, isopropyl, butyl, isobutyl, s-butyl, t-butyl, pentyl, hexyl and the like), a halogeno-lower ($C_{1-6}$) alkyl group (for example, $CF_3$, $CF_2CF_3$, $CH_2F$, $CHF_2$ and the like), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The lower acyl group of (14) described above may for example be a lower acyl group derived from a carboxylic acid, a sulfinic acid or a sulfonic acid.

The lower acyl group derived from a carboxylic acid may for example be a lower ($C_{1-6}$) alkyl-carbonyl(alkanoyl) (for example, formyl, acetyl, propionyl, butyryl, isobutyryl, valeryl, pivaloyl and the like), a $C_{3-6}$ cycloalkyl-carbonyl (for example, cyclopropylcarbonyl, cyclobutylcarbonyl, cyclopentylcarbonyl, cyclohexylcarbonyl and the like), benzoyl and the like.

The lower acyl group derived from a sulfinic acid may for example be a lower ($C_{1-6}$) alkylsulfinyl (for example, methylsulfinyl, ethylsulfinyl, propylsulfinyl, isopropylsulfinyl, butylsulfinyl, isobutylsulfinyl, s-butylsulfinyl, t-butylsulfinyl, pentylsulfinyl, hexylsulfinyl and the like), a $C_{3-6}$ cycloalkylsulfinyl (for example, cyclopropylsulfinyl, cyclobutylsulfinyl, cyclopentylsulfinyl, cyclohexylsulfinyl and the like), phenylsulfinyl and the like.

The lower acyl group derived from a sulfonic acid may for example be a lower ($C_{1-6}$) alkylsulfonyl (for example, methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, hexylsulfonyl and the like), a $C_{3-6}$ cycloalkylsulfonyl (for example, cyclopropylsulfonyl, cyclobutylsulfonyl, cyclopentylsulfonyl, cyclohexylsulfonyl and the like), phenylsulfonyl and the like.

Each "lower acyl group" exemplified above may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkyl group (for example, methyl, ethyl, propyl, isopropyl, butyl, isobutyl, s-butyl, t-butyl, pentyl, hexyl and the like), a halogeno-lower ($C_{1-6}$) alkyl group (for example, $CF_3$, $CF_2CF_3$, $CH_2F$, $CHF_2$ and the like), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The optionally substituted phenyl group of (15) described above may be substituted in any possible position by 1 to 3 same or different substituents selected from the group consisting of a halogen atom (for example, chlorine, bromine, fluorine, iodine and the like), a hydroxyl group, a nitro group, a cyano group, a lower ($C_{1-6}$) alkyl group (for example, methyl, ethyl, propyl, isopropyl, butyl, isobutyl, s-butyl, t-butyl, pentyl, hexyl and the like), a halogeno-lower ($C_{1-6}$) alkyl group (for example, $CF_3$, $CF_2CF_3$, $CH_2F$, $CHF_2$ and the like), a lower (C16) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkoxy group (for example, $CF_3O$, $CHF_2O$ and the like) and the like.

The divalent hydrocarbon group of (16) described above may for example be the groups represented by formulae:

—CH=CH—CH=CH—,

—CH=CH—CH$_2$—CH$_2$—,

—CH$_2$—CH=CH—CH$_2$—,

—CH=CH—CH$_2$—,

—(CH$_2$)$_a$— (wherein a is 3 or 4).

The divalent hydrocarbon group described above taken together with 2 ring-constituting atoms in Ring A forms a 5- or 6-membered ring, which may be substituted in any possible position by 1 to 3 same or different substituents selected from the group consisting of a lower ($C_{1-6}$) alkyl group (for example, methyl, ethyl, propyl, isopropyl, butyl, isobutyl, s-butyl, t-butyl, pentyl, hexyl and the like), a halogen atom (for example, chlorine, bromine, fluorine, iodine and the like), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy and the like), a halogeno-lower ($C_{1-6}$) alkyl group (for example, $CF_3$, $CF_2CF_3$, $CH_2F$, $CHF_2$ and the like), a halogeno-lower ($C_{1-6}$) alkoxy group (for example, $CF_3O$, $CF_2CF_3O$, $CH_2FO$, $CHF_2O$ and the like), a lower ($C_{1-6}$) alkoxy-carbonyl (for example, methoxycarbonyl, ethoxycarbonyl, propoxycarbonyl, isopropoxycarbonyl, butoxycarbonyl, s-butoxycarbonyl, t-butoxycarbonyl, pentyloxycarbonyl, isopentyloxycarbonyl, neopentyloxycarbonyl, hexyloxycarbonyl and the like), a cyano group, a nitro group, a hydroxyl group and the like.

The substituent on Ring A is preferably be an optionally halogenated lower ($C_{1-6}$) alkyl group (preferably methyl), an optionally halogenated lower ($C_{1-6}$) alkoxy group (preferably methoxy) and the like, with a lower ($C_{1-6}$) alkyl group (preferably methyl) being more preferred. Preferred Ring A may for example be a ring represented by the formula:

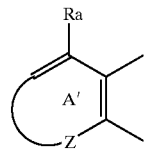

wherein A' is a 5- or 6-membered aromatic heterocyclic ring which may further have substituents in addition to substituent Ra (preferably pyridine, pyrazole, pyrrole, furan, more preferably pyridine, pyrazole and the like), Z is an oxygen atom, a sulfur atom or a nitrogen atom, Ra is a substituent on Ring A described above (preferably an optionally halogenated lower ($C_{1-6}$) alkyl group, an optionally halogenated lower ($C_{1-6}$) alkoxy group and the like).

The substituent on Ring B is preferably be a halogen atom (preferably chlorine and the like), an optionally halogenated lower ($C_{1-6}$) alkyl (preferably methyl and the like), a hydroxyl group, an optionally halogenated lower ($C_{1-6}$) alkoxy group (preferably methoxy and the like), with a halogen atom (preferably chlorine and the like) and a lower ($C_{1-6}$) alkyl group being preferred especially. Preferred Ring B may for example be a ring represented by the formula:

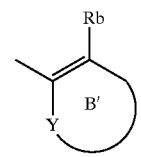

wherein B' is a 5- or 6-membered aromatic homo- or heterocyclic ring which may further have substituents in addition to substituent Rb (preferably benzene, thiophene and the like), Y is a carbon atom, an oxygen atom, a sulfur atom or a nitrogen atom, Rb is a hydrogen atom or a substituent on Ring B described above (preferably a halogen atom, an optionally halogenated lower ($C_{1-6}$) alkyl group, a hydroxyl group, an optionally halogenated lower ($C_{1-6}$) alkoxy group and the like).

In the formula (I) shown above, $R^1$ is a hydrogen atom, a hydroxyl group or a lower alkyl group (for example, a lower ($C_{1-6}$) alkyl group (for example, methyl, ethyl, propyl, isopropyl, butyl, isobutyl, s-butyl, t-butyl, pentyl, hexyl and the like), preferably methyl and the like. $R^1$ is preferably a hydrogen atom, a hydroxyl group and a methyl group, more preferably a hydrogen atom and a hydroxyl atom, especially a hydrogen atom.

In the formula (I) shown above, n is 0 or 1 (preferably 1).

Preferred Compound (I) may for example be a compound represented by the formula:

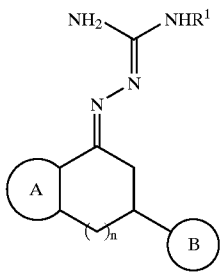

wherein each symbol is defined as described above or a salt thereof, and more preferable one is a compound represented by the formula:

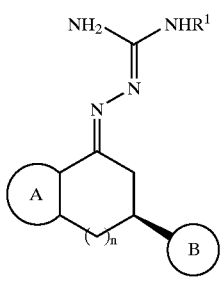

wherein each symbol is defined as described above or a salt thereof.

In a preferred example of Compound (I), Ring A is a 5-or 6-membered nitrogen-containing aromatic heterocyclic ring containing 1 or 2 nitrogen atoms which may be substituted by an optionally halogenated $C_{1-6}$ alkyl or an optionally halogenated $C_{1-6}$ alkoxy, Ring B is a 5- or 6-membered nitrogen-containing aromatic homo- or heterocyclic ring containing one heteroatom selected from oxygen, sulfur and nitrogen atoms which may be substituted by a halogen atom, an optionally halogenated $C_{1-6}$ alkyl, a hydroxyl group or an optionally halogenated $C_{1-6}$ alkoxy, $R^1$ is a hydrogen atom or a hydroxyl group, and n is 1.

Typically, preferred Compound (I) is:

(S)-(−)-7-(2,5-dichlorothiophen-3-yl)-5-guanidinoimino-4-methyl-5,6,7,8-tetrahydroquinoline, (±)-7-(2,5-dichlorothiophen-3-yl)-5-guanidinoimino-4-methyl-5,6,7,8-tetrahydroquinoline, (S)-(−)-7-(2-chlorophenyl)-5-guanidinoimino-4-methyl-5,6,7,8-tetrahydroquinoline, (±)-7-(2-chlorophenyl)-5-guanidinoimino-4-methyl-5,6,7,8-tetrahydroquinoline, (±)-7-(2-bromophenyl)-5-guanidinoimino-4-methyl-5,6,7,8-tetrahydroquinoline, 7-(3,5-dichlorothiophen-2-yl)-5-guanidinoimino-4-methyl-5,6,7,8-tetrahydroquinoline, 7-(2,5-dichlorophenyl)-5-guanidinoimino-4-methyl-5,6,7,8-tetrahydroquinoline, 6-(2,5-dichlorothiophen-3-yl)-4-guanidinoimino-3-methyl-4,5,6,7-tetrahydroindazole, (±)-7-(2,5-dichlorophenyl)-5-guanidinoimino-4-methyl-5,6,7,8-tetrahydrocinnoline, (±)-7-(5-chloro-2-methylphenyl)-5-guanidinoimino-4-methyl-5,6,7,8-tetrahydroquinoline, (±)-7-(5-fluoro-2-methylphenyl)-5-guanidinoimino-4-methyl-5,6,7,8-tetrahydroquinoline, (S)-(−)-7-(5-fluoro-2-methylphenyl)-5-guanidinoimino-4-methyl-5,6,7,8-tetrahydroquinoline, (±)-7-(2-chloro-5-fluorophenyl)-5-guanidinoimino-4-methyl-5,6,7,8-tetrahydroquinoline, (S)-(−)-7-(2-chloro-5-fluorophenyl)-5-guanidinoimino-4-methyl-5,6,7,8-tetrahydroquinoline, (±)-7-(5-chloro-2-fluorophenyl)-5-guanidinoimino-4-methyl-5,6,7,8-tetrahydroquinoline, (±)-7-(5-fluoro-2-methylphenyl)-5-guanidinoimino-4-methyl-5,6,7,8-tetrahydrocinnoline, (±)-7-(5-chloro-2-fluorophenyl)-5-guanidinoimino-4-methyl-5,6,7,8-tetrahydrocinnoline or a salt thereof, and, among them, one preferred especially is:

(S)-(−)-7-(2,5-dichlorothiophen-3-yl)-5-guanidinoimino-4-methyl-5,6,7,8-tetrahydroquinoline, (±)-7-(2,5-dichlorothiophen-3-yl)-5-guanidinoimino-4-methyl-5,6,7,8-tetrahydroquinoline, (S)-(−)-7-(2-chlorophenyl)-5-guanidinoimino-4-methyl-5,6,7,8-tetrahydroquinoline, (±)-7-(2-chlorophenyl)-5-guanidinoimino-4-methyl-5,6,7,8-tetrahydroquinoline, (±)-7-(2,5-dichlorophenyl)-5-guanidinoimino-4-methyl-5,6,7,8-tetrahydrocinnoline, (±)-7-(5-chloro-2-methylphenyl)-5-guanidinoimino-4-methyl-5,6,7,8-tetrahydroquinoline, (±)-7-(5-fluoro-2-methylphenyl)-5-guanidinoimino-4-methyl-5,6,7,8-tetrahydroquinoline, (S)-(−)-7-(5-fluoro-2-methylphenyl)-5-guanidinoimino-4-methyl-5,6,7,8-tetrahydroquinoline, (±)-7-(2-chloro-5-fluorophenyl)-5-guanidinoimino-4-methyl-5,6,7,8-tetrahydroquinoline, (S)-(−)-7-(2-chloro-5-fluorophenyl)-5-guanidinoimino-4-methyl-5,6,7,8-tetrahydroquinoline, (±)-7-(5-chloro-2-fluorophenyl)-5-guanidinoimino-4-methyl-5,6,7,8-tetrahydroquinoline, (±)-7-(5-fluoro-2-methylphenyl)-5-guanidinoimino-4-methyl-5,6,7,8-tetrahydrocinnoline, (±)-7-(5-chloro-2-fluorophenyl)-5-guanidinoimino-4-methyl-5,6,7,8-tetrahydrocinnoline or a salt thereof, and, in particular, one preferred is:

(S)-(−)-7-(2-chlorophenyl)-5-guanidinoimino-4-methyl-5,6,7,8-tetrahydroquinoline or a salt thereof (preferably dimethanesulfonate), (±)-7-(2-chlorophenyl)-5-guanidinoimino-4-methyl-5,6,7,8-tetrahydroquinoline or a salt thereof (preferably dimethanesulfonate), (±)-7-(5-fluoro-2-methylphenyl)-5-guanidinoimino-4-methyl-5,6,7,8-tetrahydroquinoline or a salt thereof, (S)-(−)-7-(5-fluoro-2-methylphenyl)-5-guanidinoimino-4-methyl-5,6,7,8-tetrahydroquinoline or a salt thereof, (±)-7-(2-chloro-5-fluorophenyl)-5-guanidinoimino-4-methyl-5,6,7,8-tetrahydroquinoline or a salt thereof, and, (S)-(−)-7-(2-chloro-5-fluorophenyl)-5-guanidinoimino-4-methyl-5,6,7,8-tetrahydroquinoline or a salt thereof, and one employed advantageously is (S)-(−)-7-(2-chlorophenyl)-5-guanidinoimino-4-methyl-5,6,7,8-tetrahydroquinoline or a salt thereof (preferably dimethanesulfonate), and, when used as a nasal preparation, those preferred especially are (S)-(−)-7-(5-fluoro-2-methylphenyl)-5-guanidinoimino-4-methyl-5,6,7,8-tetrahydroquinoline or a salt thereof, and (S)-(−)-7-(2-chloro-5-fluorophenyl)-5-guanidinoimino-4-methyl-5,6,7,8-tetrahydroquinoline or a salt thereof (preferably dimethanesulfonate).

Compound (I) may be present as a prodrug, which means a compound capable of being converted into Compound (I) as a result of an in vivo reaction for example with an enzyme under a physiological condition, i.e., a compound capable of being converted into Compound (I) as a result of an enzymatic oxidation, reduction, hydrolysis and the like. The prodrug of Compound (I) may for example a compound formed as a result of acylation, alkylation or phosphorylation of an amino group of Compound (I) (for example, a compound formed as a result of eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, t-butylation of an amino group of Compound (I)), a compound formed as a result of acylation, alkylation, phosphorylation and boration of a hydroxyl group of Compound (I) (for example, a compound formed as a result of acetylation, palmitoylation, propanoylation, pivaloylation, succinylation, fiunarylation, alanylation, dimethylaminomethylcarbonylation of a hydroxyl group of Compound (I)), or a compound formed as a result of esterification and amidation of a carboxyl group of Compound (I) (for example, a compound formed as a result of ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, methyl amidation and the like of a carboxyl group of Compound (I)). Any of these compounds can be produced by a method known per se from Compound (I).

The prodrug of Compound (I) may also be a compound which is converted into Compound (I) under a physiological condition described in "Development of pharmaceuticals (IYAKUHINNNOKAIHATSU)", Vol.7, Molecule design, pages 163 to 198, published by HIROKAWA SHOTEN in 1990.

Compound (I) and a synthetic intermediate salt thereof may for example be a pharmaceutically acceptable salt including an inorganic salt such as hydrochloride, hydrobromide, sulfate, nitrate and phosphate, an organic salt such as acetate, tartarate, citrate, fumarate, maleate, toluenesulfonate and methanesulfonate, a salt with an amino acid such as aspartic acid, glutamic acid, pyroglutamic acid, arginine, lysine and ornithine, a salt with a metal such as sodium, potassium, calcium and aluminium, a salt with a base such as triethylamine, guanidine, ammonium, hydrazine, quinine, cinchonine and the like.

Compound (I) may be a hydrate or an anhydrous.

When Compound (I) is present as a configuration isomer, diastereomer, conformer and the like, it can be isolated if desired by a separation/purification method known per se.

Compound (I) shows a geometrical isomerism on the basis of the steric configuration in relation to the fused heterocyclic ring containing Ring A in a hydrazone structure moiety, and can be present as an E or Z isomer as well as a mixture thereof. In addition, it also shows a geometrical isomerism on the basis of the double bond of a guanidino group when $R^1$ denotes a hydroxyl group or a lower alkyl group, and can be present as an E or Z isomer as well as a mixture thereof. The compound according to the present invention encompasses the following individual isomers and mixtures thereof.

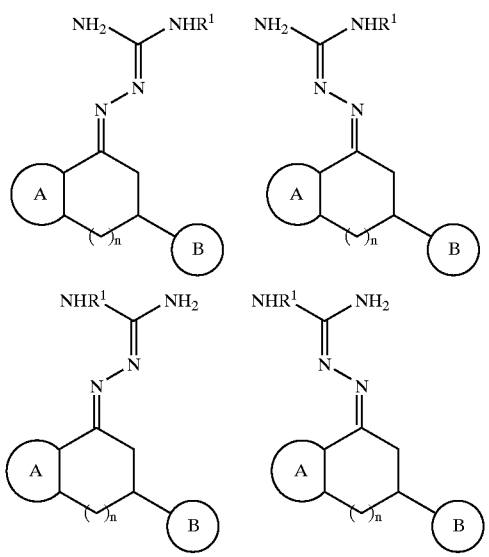

Compound (I) also shows an optical isomerism on the basis of an asymmetric carbon atom present for example in the moiety where Ring B is substituted, and can be present, with regard to each asymmetric carbon atom, as an R or S isomer as well as a mixture thereof. These isomers can be separated to individual R and S forms by ordinary optical resolution method, and the respective optical isomers and racemates are also included in the invention. For example, the compound according to the present invention encompasses the following individual optical isomers and mixtures thereof.

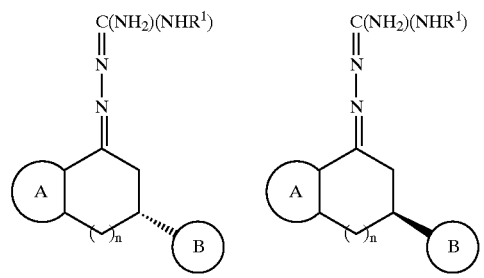

In the present invention, a starting compound for Compound (I) or a synthetic intermediate or a salt thereof may sometimes be abbreviated as Compound (I) or a synthetic intermediate by omitting the expression "or a salt thereof".

Compound (I) is equivalent structurally to Compound (Ia) and Compound (Ib).

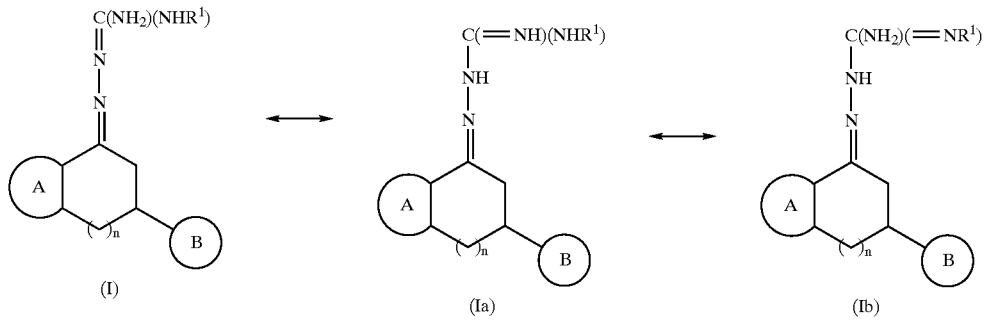

Compound (I) can be synthesized by a method in accordance with those described for example in JP-A-7-309837, Japanese Patent Application No.9-224945 (JP-A-10-114753), Japanese Patent Application No.9-224946 (JP-A-10-114744) and the like, or can be synthesized also by reacting a compound represented by the formula (II):

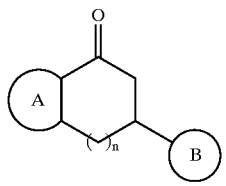

wherein symbols are defined as described above or a salt thereof with an aminoguanidine compound represented by Formula (III): $H_2N-N=C(NH_2)(NHR_1)$ wherein symbols are defined as described above or a salt thereof.

Compound (III) is employed usually in an amount of about 1 mole to about 2 moles per 1 mole of Compound (II). This reaction can be promoted if necessary by adding an about 1/10- to about 10-fold molar amount of triethylamine, pyrrolidine, sodium acetate, boron trifluoride/diethylether, hydrochloric acid, sulfuric acid, p-toluenesulfonic acid and the like as a catalyst.

For example, this condensation reaction can be performed in an inert solvent such as methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), acetic acid, pyridine, water and the like, as well as a mixture thereof. The reaction temperature is within the range from about 0° C. to about 180° C.

Compound (II) and Compound (III) employed as starting materials can be produced by or in accordance with known methods, and can be produced for example by a method shown in Scheme I or a method described below in Reference Example.

Scheme I

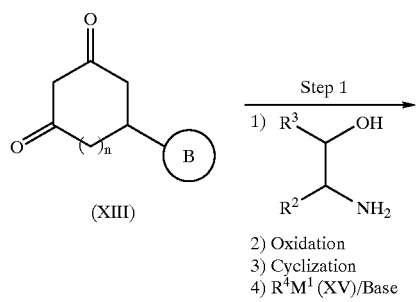

-continued

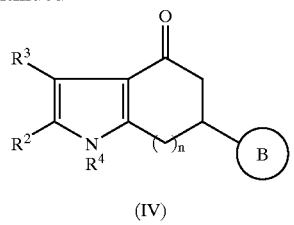

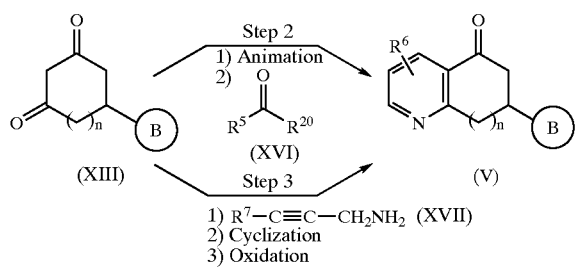

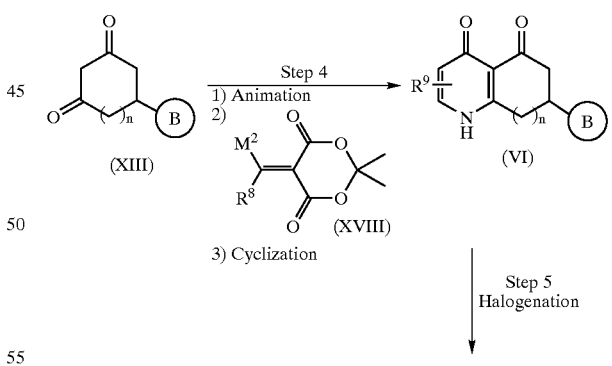

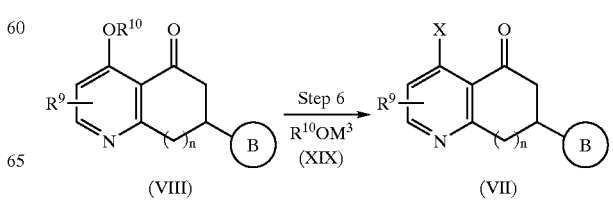

-continued

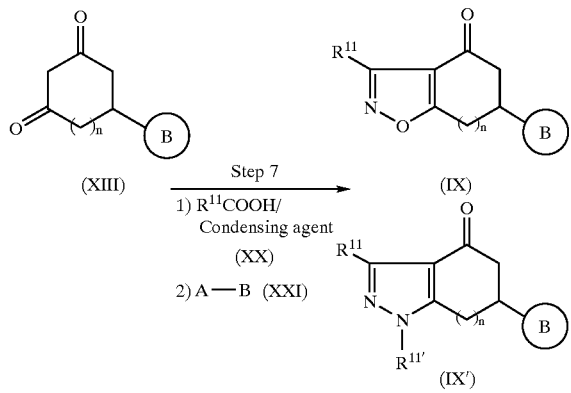

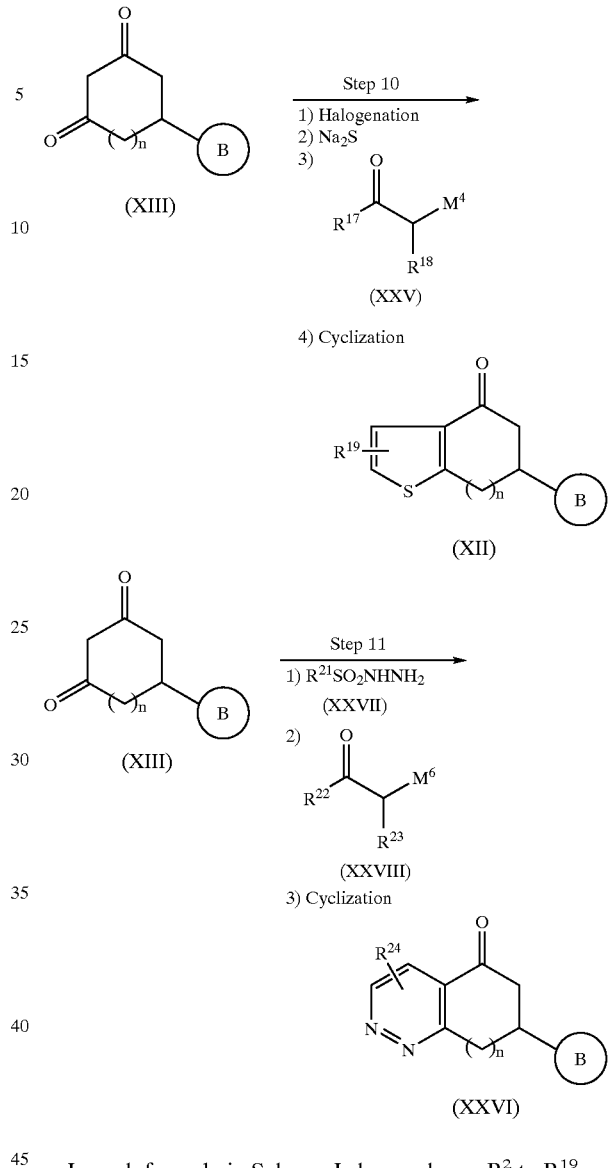

In each formula in Scheme I shown above, $R^2$ to $R^{19}$ and $R^{22}$ to $R^{24}$ are the substituents on Ring A and $M^1$ to $M^6$ are leaving groups.

Each step is detailed below.

(Step 1)

After reacting Compound (XIII) with Compound (XIV), the hydroxyl group is oxidized to effect a cyclization, whereby producing the ketone compound (IV). If necessary, the cyclization product is reacted with Compound (XV) in the presence of a base to introduce Substituent $R^4$ into the ketone compound, whereby producing Compound (IV).

This condensation reaction is performed in an inert solvent such as tetrahydrofuran, diethylether, dimethoxyethane, methanol, ethanol, hexane, toluene, benzene, dichloromethane, acetic acid or a mixture thereof at a temperature within the range from about 0° C. to about 130° C. The reaction time ranges from about 1 hour to about 100 hours. Compound (XIV) is employed in an amount usually of about 1 to about 2 moles per 1 mole of Compound (XIII). The reaction can be promoted for example by adding a molecular sieve.

Subsequent oxidation, cyclization or dehydration may be effected in a procedure known per se for example by a method in which an equimolar or about 2-fold molar amount of an aromatic halide is employed as an oxidizing agent in the presence of about 0.1 to about 20% by moles of a transition metal catalyst and one equivalent to about 2-fold molar amount of a base in an inert solvent such as tetrahydrofuran, dimethoxyethane, dimethylformamide, N-methylpyrrolidone, hexane, toluene, benzene, dichloromethane, chloroform or a mixture thereof at a temperature within the range from about 50° C. to about 200° C. The reaction time ranges from about 1 hour to about 50 hours. The aromatic halide employed as the oxidizing agent may for example be bromobenzene, bromomesitylene, o-bromotoluene and the like. The transition metal catalyst may for example be nickel, palladium, platinum, ruthenium, and the reaction can be promoted by using a palladium catalyst such as tetrakis(triphenylphosphine) palladium. As the base, potassium carbonate and sodium hydride can be exemplified. This reaction is performed for example under an inert gas atmosphere (for example, nitrogen, argon).

The reaction with Compound (XV) is performed in an inert solvent such as tetrahydrofuran, dimethoxyethane, dimethylformamide, N-methylpyrrolidone, hexane, toluene, benzene, dichloromethane, chloroform or a mixture thereof at a temperature within the range from about 0° C. to about 150° C. The reaction time ranges from about 1 hour to 5 hours. The base which can be employed is triethylamine, lithium hydride, sodium hydride, sodium methoxide, sodium ethoxide, potassium t-butoxide and the like. Compound (XV) is employed in an amount usually of about 1 to about 2 moles per 1 mole of Compound (XIII).

(Step 2)

Compound (XIII) is reacted with an aminating agent to form an enamine derivative, which is then reacted with Compound (XVI) (wherein $R^{20}$ is —$CH_2COCH_3$, —$C\equiv CH$, —$CH_2CH(OMe)_2$ and the like) to form the ketone compound (V). Alternatively, Compound (XIII) is reacted with Compound (XVI) if necessary in the presence of an aminating agent to produce the ketone compound (V) without isolating an enamine derivative.

The amination is performed in the presence of an aminating agent such as ammonium acetate in an inert solvent such as methanol, ethanol, benzene, toluene, chloroform, dichloromethane, 1,2-dichloroethane, tetrahydrofuran, diethyl ether, hexane, ethyl acetate, dimethylformamide and the like as well as a mixture thereof at a temperature within the range from about 0° C. to about 150° C. The reaction time ranges from about 1 hour to about 100 hours. The aminating agent is employed in an amount usually of about 1 to about 10 moles per 1 mole of Compound (XIII).

The condensation and cyclization reaction is performed in an inert solvent such as methanol, ethanol, benzene, toluene, chloroform, dichloromethane, 1,2-dichloroethane, tetrahydrofuran, diethyl ether, hexane, ethyl acetate, dimethylformamide, dimethylsulfoxide and the like as well as a mixture thereof at a temperature within the range from about 0° C. to about 150° C. The reaction time ranges from about 1 hour to about 50 hours. Compound (XVI) is employed in an amount usually of about 1 to about 5 moles per 1 mole of Compound (XIII).

Also when the enamine derivative is not isolated, the reaction is performed similarly in the presence of the aminating agent such as ammonium acetate.

(Step 3)

After reacting Compound (XIII) with Compound (XVII), cyclization and oxidation are performed to produce the ketone compound (V).

This condensation reaction is performed in an inert solvent such as tetrahydrofuran, diethylether, dimethoxyethane, methanol, ethanol, hexane, toluene, benzene, dichloromethane or a mixture thereof at a temperature within the range from about 0° C. to about 130° C. The reaction time ranges from about 1 hour to about 100 hours. Compound (XVII) is employed in an amount usually of about 1 to about 2 moles per 1 mole of Compound (XIII).

Subsequent cyclization and oxidation are performed without any solvent or in an inert solvent such as diphenyl ether, tetrahydrofuran, dimethylformamide, dimethylsulfoxide, xylene, toluene or a mixture thereof in an air (or under an oxygen atmosphere) at room temperature to about 300° C. The reaction time ranges from about 1 hour to about 10 hours.

(Step 4)

After reacting Compound (XIII) with the aminating agent, the reaction with Compound (XVIII) followed by cyclization results in the ketone compound (VI).

The amination is performed similarly to Step 2.

The subsequent condensation reaction is performed in an inert solvent such as methanol, ethanol, benzene, toluene, chloroform, dichloromethane, 1,2-dichloroethane, tetrahydrofuran, diethyl ether, hexane, ethyl acetate, dimethylformamide, dimethylsulfoxide and the like as well as a mixture thereof at a temperature within the range from about 0° C. to about 100° C. The reaction time ranges from about 1 hour to about 50 hours. Compound (XVIII) is employed in an amount usually of about 1 to about 2 moles per 1 mole of Compound (XIII).

The subsequent cyclization reaction is performed without any solvent or in an inert solvent such as tetrahydrofuran, diphenyl ether, dimethoxyethane, methanol, ethanol, dichloromethane, chloroform, hexane, benzene, toluene and the like or a mixture thereof at about 50° C. to about 300° C. The reaction time ranges from about 10 minutes to about 5 hours.

(Step 5)

By halogenating Compound (VI) produced in Step 4, the ketone compound (VII) (wherein X is a halogen atom) can be produced.

The halogenation can be performed in a procedure known per se for example by a method in which phosphorus oxychloride is employed as a halogenating agent in an about 1- to about 20-fold amount without any solvent or in an inert solvent such as tetrahydrofuran, dimethoxyethane, hexane, toluene, benzene, dichloromethane, chloroform or a mixture thereof at a temperature of about 0° C. to about 150° C. The reaction time ranges from about 30 minutes to about 10 hours. The reaction can be promoted for example by adding dimethylformamide.

(Step 6)

By reacting Compound (VII) produced in Step 5 with Compound (XIX), the ketone compound (VIII) can be produced.

The reaction is performed in an inert solvent such as tetrahydrofuran, diethyl ether, dimethoxyethane, methanol, ethanol, hexane, toluene, benzene, dichloromethane, chloroform, dimethylformamide, dimethylsulfoxide or a mixture thereof at a temperature within the range from about 0° C. to about 150° C. The reaction time ranges from about 30 minutes to about 50 hours. While Compound (XIX) is employed usually in an amount of about 1 to about 2 moles per 1 mole of Compound (VII), it can be employed also as a solvent. If necessary, a base such as lithium hydride, sodium hydride, sodium methoxide, sodium ethoxide and potassium t-butoxide can be employed.

(Step 7)

After reacting Compound (XIII) with Compound (XX), Compound (XXI) (wherein A–B is an optionally substituted hydrazine, hydroxylamine and the like) is reacted and cyclized to produce the ketone compound (IX) or (IX').

The condensation reaction is performed by a method known per se in the presence of a condensing agent such as DDC and WSC in an inert solvent such as tetrahydrofuran, diethylether, dimethoxyethane, dimethylformamide, dimethylsulfoxide, hexane, toluene, benzene, dichloromethane, chloroform, ethyl acetate or a mixture thereof, while serving as a base, at a temperature within the range from about 0° C. to about 150° C. The reaction time ranges from about 1 hour to about 50 hours. Compound (XX) is employed usually in an amount of about 1 to 3 moles per 1 mole of Compound (XIII).

The subsequent cyclization reaction is performed in an inert solvent such as tetrahydrofuran, diphenyl ether, dimethoxyethane, methanol, ethanol, hexane, toluene, benzene, dichloromethane, chloroform, dimethylformamide, dimethylsulfoxide or a mixture thereof at a temperature within the range from about 0° C. to about 150° C. The reaction time ranges from about 1 hour to about 50 hours. Compound (XXI) is employed usually in an amount of about 1 to 2 moles per 1 mole of Compound (XIII).
(Step 8)

After reacting Compound (XIII) with Compound (XXII), Compound (XXIII) is reacted and cyclized to produce the ketone compound (X).

The condensation reaction is performed by a method similar to that employed in the condensation in Step 7.

The subsequent cyclization reaction is performed in an inert solvent such as tetrahydrofuran, diphenyl ether, dimethoxyethane, methanol, ethanol, hexane, benzene, toluene, dichloromethane, chloroform, dimethylformamide, dimethylsulfoxide or a mixture thereof at a temperature within the range from about 0° C. to about 150° C. The reaction time ranges from about 1 hour to about 100 hours. This reaction can be promoted when the product of the first condensation reaction is reacted with an amine to form an enamine derivative which is then reacted with Compound (XXII).
(Step 9)

After reacting Compound (XIII) with Compound (XXIV), a cyclization is performed to produce the ketone compound (XI).

This condensation reaction is performed in an inert solvent such as tetrahydrofuran, diethyl ether, dimethoxyethane, methanol, ethanol, hexane, toluene, benzene, dichloromethane, chloroform, dimethylformamide, dimethylsulfoxide or a mixture thereof in the presence of a base at a temperature within the range from about 0° C. to about 100° C. The reaction time ranges from about 30 minutes to about 20 hours. The base which can be employed may for example be lithium hydride, sodium hydride, sodium methoxide, sodium ethoxide, potassium t-butoxide and the like. Compound (XXIV) is employed usually in an amount of about 1 to 2 moles per 1 mole of Compound (XIII).

The subsequent cyclization reaction is performed without any solvent or in an inert solvent such as tetrahydrofuran, diphenyl ether, dimethoxyethane, methanol, ethanol, dimethylformamide, dimethylsulfoxide, xylene, toluene, dichloromethane, chloroform and the like or a mixture thereof at room temperature to about 300° C. The reaction time ranges from about 1 hour to about 50 hours.
(Step 10)

After Compound (XIII) is halogenated, it is reacted for example with Na$_2$S and the resultant product is then reacted with Compound (XXV) to effect cyclization, whereby producing the ketone compound (XII).

The halogenation can be effected in a procedure known per se for example by a method in which phosphorus trichloride is employed as a halogenating agent in an about 1/3- to 5-fold molar amount without any solvent or in an inert solvent such as tetrahydrofuran, dimethoxyethane, hexane, toluene, benzene, dichloromethane, chloroform or a mixture thereof at a temperature within the range from about 0° C. to about 150° C. The reaction time ranges from about 30 minutes to about 10 hours.

The reaction for example with Na$_2$S is performed in an inert solvent such as water, tetrahydrofuran, diethyl ether, dimethoxyethane, methanol, ethanol, hexane, toluene, benzene, dichloromethane, chloroform or a mixture thereof at a temperature within the range from about 0° C. to about 100° C. The reaction time ranges from about 30 minutes to about 10 hours.

The condensation reaction is performed in an inert solvent such as such as tetrahydrofuran, diethyl ether, dimethoxyethane, methanol, ethanol, hexane, toluene, benzene, dichloromethane, chloroform, dimethylformamide, dimethylsulfoxide or a mixture thereof at a temperature within the range from about 0° C. to about 100° C. The reaction time ranges from about 30 minutes to about 20 hours. The base which can be employed may for example be lithium hydride, sodium hydride, sodium methoxide, sodium ethoxide, potassium t-butoxide and the like. Compound (XXV) is employed usually in an amount of about 1 to 2 moles per 1 mole of Compound (XIII).

The subsequent cyclization reaction is performed without any solvent or in an inert solvent such as tetrahydrofuran, diphenyl ether, dimethoxyethane, methanol, ethanol, dimethylformamide, dimethylsulfoxide, xylene, toluene, dichloromethane, chloroform and the like or a mixture thereof at room temperature to about 300° C. The reaction time ranges from about 1 hour to about 100 hours.
(Step 11)

After Compound (XIII) is reacted with Compound (XXVII) (wherein R21 is an optionally substituted phenyl such as phenyl, 4-methylphenyl, 4-methoxyphenyl and the like) to form a hydrazide derivative, it is reacted with Compound (XXVIII) in the presence of a base to produce the ketone compound (XXVI).

The reaction with Compound (XXVII) is performed in an inert solvent such as methanol, ethanol, toluene, benzene, dichloromethane, chloroform, 1,2-dichloromethane, tetrahydrofuran, diethylether, hexane, ethyl acetate, dimethylformamide, or a mixture thereof at a temperature within the range from about 0° C. to about 150° C. The reaction time ranges from about 1 hour to about 100 hours. The aminating agent is used usually in an amount of about 1 to about 10 moles per 1 mole of Compound (XIII).

The reaction with Compound (XXVIII) and cyclization are performed in an inert solvent such as methanol, ethanol, toluene, benzene, dichloromethane, chloroform, 1,2-dichloroethane, tetrahydrofuran, diethyl ether, hexane, ethyl acetate, dimethylformamide, dimethylsulfoxide, or a mixture thereof at a temperature within the range from about 0° C. to about 150° C. The reaction time ranges from about 1 hour to 50 hours. The base which can be employed is potassium carbonate, lithium hydride, sodium hydride, sodium methoxide, sodium ethoxide, potassium t-butoxide and the like. Compound (XXVIII) is employed in an amount usually of about 1 to about 5 moles per 1 mole of Compound (XIII).

The ketone compound obtained in any of Steps 1 to 11 can be employed in the next step without isolation or purification.

When the compound has a carbonyl group, an amino group, a hydroxyl group or a carboxyl group in any of the production methods described above, an ordinary protective group may previously be introduced into the compound by a method known per se and it may be removed if necessary after the reaction to obtain an intended product.

A protective group for the carbonyl group employed here may for example be an optionally substituted cyclic or acyclic acetal or ketal, an optionally substituted cyclic or acyclic dithioacetal or dithioketal.

A protective group for the amino group employed here may for example be a lower ($C_{1-6}$) alkyl-carbonyl (for example, formyl, acetyl, propionyl, butyryl, isobutyryl, valeryl, pivaloyl and the like) and benzoyl.

A protective group for the hydroxyl group may for example be methoxydimethylmethyl, trimethylsilyl, t-butyldimethylsilyl, trimethylsilylethoxymethyl, (SEM), methoxymethyl, benzyloxymethyl and tetrahydropyranyl (THP).

A protective group for the carboxyl group may for example be a lower ($C_{1-6}$) alkyl (for example, methyl, ethyl, propyl, isopropyl, butyl, isobutyl, s-butyl, t-butyl, pentyl, hexyl and the like), a $C_{7-12}$ aralkyl (for example, benzyl, phenethyl, 4-phenylpropyl, 4-phenylbutyl, 1-naphthylmethyl and the like). The carboxyl group may be protected also as being converted into a 2-oxazoline ring.

While a method for introducing and cleaving a protective group may be in accordance (with a method known per se (for example, a method described in Protective Groups in Organic Chemistry, J. F. W. McOmie et al., Plenum Press), a cleavage may also be accomplished using acids, base, reductions, ultraviolet light, hydrazine, phenylhydrazine, sodium N-methyldithiocarbamate, tetrabutylammonium fluoride, palladium acetate and the like.

Among the starting compounds and the synthetic intermediates for Compound (I) described above, a basic compound can be converted into a salt using an acid in accordance with a standard method. A suitable acid for this reaction is preferably an acid which gives a pharmaceutically acceptable salt. Those which can be exemplified are inorganic acids such as hydrochloric acid, hydrobromic acid, phosphoric acid, sulfuric acid, nitric acid and sulfamic acid as well as organic acids such as acetic acid, tartaric acid, citric acid, fumaric acid, maleic acid, p-toluenesulfonic acid, methanesulfonic acid, glutamic acid and pyroglutamic acid. When a resultant compound is a salt, it may be converted into a free base in accordance with a standard method.

Among the starting compounds and the synthetic intermediates for Compound (I), a compound having an acidic group such as —COOH can be converted into a salt in accordance with a standard method. Such salt is preferably a salt with an alkaline metal, an alkaline earth metal, ammonium, a substituted ammonium and the like, more typically, a salt with sodium, potassium, lithium, calcium, magnesium, aluminium, zinc, ammonium tri-$C_{1-6}$ alkylammonium (for example, trimethylammonium, triethylammonium and the like), triethanolammonium and the like.

Each reaction described above is conducted usually from equimolar amounts of respective starting materials for a period usually of 1 to 24 hours, unless otherwise specified.

Compound (I) or a starting material therefor thus obtained can be isolated from the reaction mixture by an ordinary separating and purifying procedure, such as extraction, concentration, neutralization, filtration, crystallization, recrystallization, column (or thin layer) chromatography and the like.

Compound (I) has an excellent Na—H exchange inhibitory effect and a low toxicity and a high stability.

The nasal preparation according to the present invention can be formulated using Compound (I) as an active ingredient by a method known per se, if appropriate in a mixture with an appropriate amount of a pharmaceutically acceptable carrier.

A pharmaceutically acceptable carrier may for example be a conventional organic or inorganic substance as an ingredient of a pharmaceutical preparation, such as excipient, lubricant, binder, disintegrant, vehicle, solubilizer, suspending agent, isotonicity, buffer, analgesic agent and the like. If necessary, additives such as preservative, antioxidant, colorant, sweetener, adsorbent, wetting agent and the like may also be added.

The excipient may for example be lactose, sugar, D-mannitol, starch, corn starch, crystalline cellulose, light silicic anhydride and the like.

The lubricant may for example be magnesium stearate, calcium stearate, talc, colloidal silica and the like.

The binder may for example be crystalline cellulose, sugar, D-mannitol, dextrin, hydroxypropyl cellulose, hydroxypropylmethyl cellulose, polyvinyl pyrrolidone, starch, sucrose, gelatin, methyl cellulose, sodium carboxymethyl cellulose and the like.

The disintegrant may for example be starch, carboxymethyl cellulose, calcium carboxymethyl cellulose, sodium *CROSCARMELOSE*, sodium carboxymethyl starch, L-hydroxypropyl cellulose and the like.

The vehicle may for example be water for injection, alcohol, propylene glycol, macrogol, sesame oil, corn oil and the like.

The solubilizer may for example be polyethylene glycol, propylene glycol, D-mannitol, benzyl benzoate, ethanol, trisaminomethane, cholesterol, triethanolamine, sodium carbonate, sodium citrate and the like.

The suspending agent may for example be a surfactant such as stearyl triethanolamine, sodium lauryl sulfate, laurylaminopropionic acid, lecithin, benzalkonium chloride, benzethonium chloride, glycerin monostearate and the like; a hydrophilic polymer such as polyvinyl alcohol, polyvinyl pyrrolidone, sodium carboxymehtyl cellulose, methyl cellulose, hydroxymethyl cellulose, hydroxyethyl cellulose, hydroxypropyl cellulose and the like.

The isotonicity may for example be glucose, D-sorbitol, sodium chloride, glycerin, D-mannitol and the like.

The buffer may for example be a buffer solution of phosphates, acetates, carbonates, citrates and the like.

The analgesic may for example be benzyl alcohol and the like.

The preservative may for example be p-oxybenzoate, chlorobutanol, benzyl alcohol, phenethyl alcohol, dehydroacetic acid, sorbic acid and the like.

The antioxidant may for example be sulfites and ascorbates.

More typically, the nasal preparation according to the present invention can be formulated as a powder by dispersing, adhering and binding an effective amount of Compound (I) uniformly into a physiologically acceptable particulate carrier whose mean particle size is 250 μm or less. Specifically, Compound (I) is mixed with the carrier. This mixing procedure may also be performed with exerting a pressure or a sheer stress as is often the case with a mortar.

In the present invention, the carrier into which Compound (I) is dispersed, adhered and bound is a di- or higher polyvalent metal compound, such as aluminum compounds, calcium compounds, magnesium compounds, silicon compounds, iron compounds, zinc compounds and the like, which are particulate compounds employed as pharmacologically acceptable carriers from a pharmaceutical point of view.

The calcium compound employed here as a di- or higher polyvalent metal compound may for example be calcium carbonate, apatite, hydroxyapatite, disodium calcium edetate, calcium chloride, calcium citrate, calcium gluconate, calcium glycerophosphate, calcium silicate, calcium hydroxide, calcium oxide, calcium stearate, calcium t-phosphate, calcium lactate, calcium pantothenate, calcium palmitate, calcium D-pantothenate, calcium alginate, calcium oleate, anhydrous calcium phosphate, calcium hydrogen phosphate, calcium hydrogen phosphate, calcium dihydrogen phosphate, calcium sulfate, calcium acetate, calcium saccharate, calcium p-aminosalicylate, biological lime compound and the like.

The aluminum compound may for example be chlorohydroxyaluminium, dried aluminium hydroxide gel, light alumilnium oxide, synthetic aluminium silicate, colloidal hydrated aluminium silicate, aluminium hydroxide, magnesium aluminium hydroxide, aluminium hydroxide gel, aluminium sulfate, calcium aluminium sulfate, dihydroxyaluminium acetate, aluminium stearate, aluminium monostearate, naturally-occurring aluminium silicate and the like.

The magnesium compound may for example be magnesium carbonate, magnesium chloride, magnesium oxide, magnesium hydroxide, magnesium L-aspartate, magnesium gluconate, magnesium sulfate, magnesium aluminate silicate, magnesium aluminate metasilicate, magnesium silicate, magnesium stearate, magnesium sodium silicate, synthetic magnesium sodium silicate and the like.

Examples of the silicon compound include hydrated silicon dioxide, silicon dioxide, light silicic anhydride, synthetic hydrotalcite, diatomaceous earth and the like, and examples of the iron compound include iron sulfate and the like. Examples of the zinc compound include zinc chloride, zinc oxide, zinc sulfate, zinc stearate and the like.

Each of the polyvalent metal compound may be employed alone or in combination with each other. The polyvalent compound has a mean particle size of about 250 $\mu$m or less, preferably about 100 $\mu$m or less, more preferably about 30 to about 60 $\mu$m.

Among these polyvalent metal compounds described above, a calcium compound, especially calcium carbonate, is employed preferably.

On the other hand, preferably, Compound (I) is divided particles as fine as possible.

When the nasal preparation according to the present invention is formulated as a powder, the amount of Compound (I) may for example be about 0.01 to about 100%, preferably about 0.1 to about 50%, more preferably about 1 to about 20% based on 100% by weight of the formulation. The amount of a carrier as an ingredient of the nasal preparation according to the present invention may for example be about 0 to about 99.99%, preferably about 50 to about 99.9%, more preferably about 80 to about 99% based on 100% by weight of the preparation.

When the nasal preparation according to the present invention is formulated as a liquid preparation, it can be produced by dissolving, suspending or emulsifying Compound (I) in water, physiological saline and the like to obtain a predetermined volume if necessary in combination with vehicle, solubilizing agent, suspending agent, isotonicity, buffering agent, analgesic and the like. In such case, the concentration of Compound (I) in a solution may for example be about 2 mg/ml to about 5 g/ml, preferably about 50 mg/ml to about 500 mg/ml. Since the pH of the solution after dissolution may become 3 or lower, it is preferable to use the solution after adjusting its pH within the range from pH 3 to pH 8, more preferably pH 4 to pH 7, by adding a suitable buffering agent (for example, phosphate, citrate and the like) to suppress any irritating effects on the nasal mucosa upon administration. While the compound may sometimes deposit partially to form a suspension, a suitable suspending agent (for example, sodium carboxymethyl cellulose, hydroxypropyl cellulose and the like) may be added. Sodium alginate, sodium hyaluronate or hydroxypropyl cellulose may also be added to give a viscosity, whereby prolonging a residential time.

While the amount of Compound (I) in the preparation according to the present invention may be selected depending on the activity of Compound (I) and the amount required for a treatment, it is preferably adjusted to be a usual dose or greater in a unit dosage form in view of the fact that the bioavailability is not 100% and thus the compound once administered is not always absorbed entirely. Also when the administration is performed several times repetitively from an identical container in the form for example of a liquid or an aerosol, the single dosage is preferably adjusted usually to be a dose or greater. An attention should be paid also to the difference in the dosage between the kinds or the body weights of warm-blooded animals such as human being, livestocks and the like.

While the preparation according to the present invention, when still being not opened, is stored at ambient temperature or in a cool place, it is stored preferably in a cool place. The ambient temperature or the cool place means those defined under Japanese pharmacopoeia. When the administration is performed several times repetitively from an identical container, a certain means for preventing any contamination upon administration, for example a means for preventing a countercurrent of a body fluid into the container, is desired, and a storage in a cool place is preferred. Also in order to prevent any growth of an undesirable organism in a container, a pharmaceutically acceptable preservative or antibacterial agent may be added.

The nasal preparation containing Compound (I) having an excellent Na—H exchange inhibitory activity thus obtained has low toxicity and excellent stability, because of which it can be administered safely as a medicine and exhibits an excellent Na—H exchange inhibitory activity which leads to a cell dysfunction improving effect and a cell protecting effect (especially on myocardial cell) in animals, especially in mammals (for example human, monkey, pig, dog, cat, rabbit, guinea pig, rat, mouse and the like), and thus is useful as a prophylactic or therapeutic agent for ischemic diseases (for example, myocardial infarction and accompanying dysfunctions, unstable angina and the like), restenosis after PTCA, arrhythmia, cardiac insufficiency, cardiac hypertrophy, hypertension and accompanying tissue failures, ischemic cerebral diseases (for example, cerebral disorders accompanying to cerebral infarction, cerebral hemorrhage, subarachnoid hemorrhage and the like) (preferably as a prophylactic or therapeutic agent against ischemic diseases such as myocardial infarction and accompanying dysfunctions, unstable angina and the like, restenosis after PTCA, arrhythmia, cardiac insufficiency, cardiac hypertrophy, more preferably as a prophylactic or therapeutic agent against ischemic diseases such as myocardial infarction, as a prophylactic or therapeutic agent against cardiac insufficiency). The concept of the prophylaxis of a cardiac insufficiency means here to include a treatment after a myocardial infarction, while the concept of the prophylaxis of a cardiac insufficiency means to include a prevention of the advancement or the exacerbation of the cardiac insufficiency.

While the dose of the nasal preparation according to the present invention may vary depending on the subject and the condition to be treated, a patient having a myocardial infarction (adult weighing about 60 kg) receives usually as a single dose about 0.005 to about 10 mg/kg, preferably about 0.01 to about 5 mg/kg, more preferably about 0.2 to about 3 mg/kg (about 0.3 to about 600 mg/adult, preferably about 0.6 to about 300 mg/adult, more preferably about 12 to about 180 mg/adult) as Compound (I), which is given preferably about one to about three times a day depending on the condition and the like. An acute onset of a disease, such as an acute state after the onset of a myocardial infarction, may be treated with a higher dose especially at a higher frequency, for example 4 times a day.

When the nasal preparation according to the present invention is formulated as a powder, a single dose of a powder obtained as described above is filled in a conventional capsule (for example, gelatin capsule No.2, hydroxypropyl cellulose capsule No.2 and the like), and may be administered nasally using a customary nasal powder spray container, such as Bubblizer (TEIJIN), Insufflator (PHISONS) or Jetlizer (UNICIAJEX) and the like. In such case, the dose of a powder formulation to a human ranges from about 1 to about 300 mg, preferably about 10 to about 150 mg, more preferably about 30 to about 100 mg.

When a liquid formulation is employed, Compound (I) dissolved for example in physiological saline or a vacuum-dried or freeze-dried Compound (I)-containing formulation dissolved in water or physiological saline may be infused by a sprayer or a suitable infuser. In such case, the volume of such solution to a human ranges from about 1 to about 200 µl, preferably about 10 to about 100 µl, more preferably about 30 to about 80 µl.

An active ingredient contained in the nasal preparation according to the present invention may not only be Compound (I) described above but also be any of the following Na—H inhibiting compound or NSI-1436 in an appropriate amount.

Hoe-642

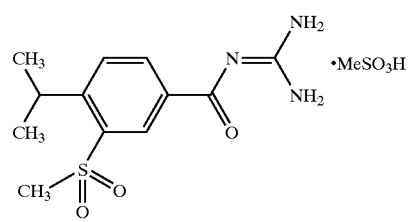

FR-168888

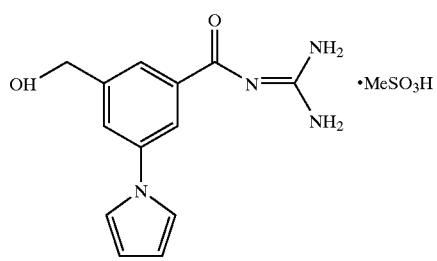

EMD-96785 (YM-103)

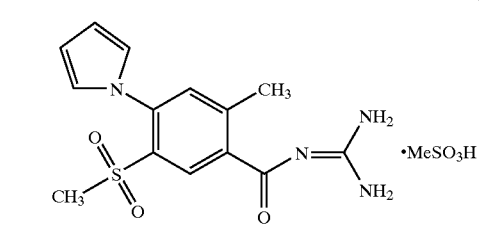

-continued

EMD 85131

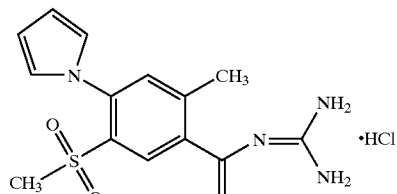

KB-R-9032

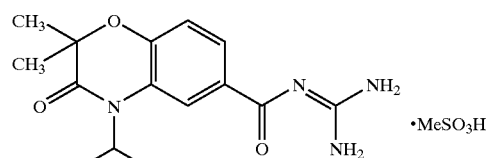

SM-20550

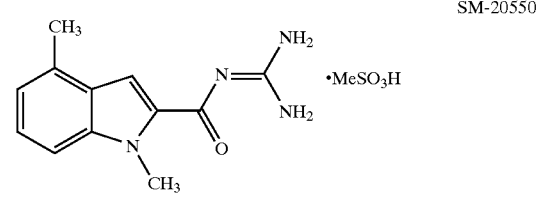

FR-183998

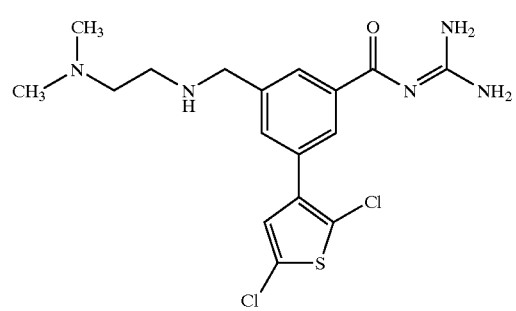

SM-20220

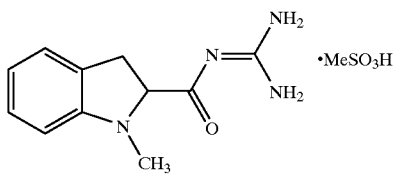

Compound Described in DE-19712636 TY-12533

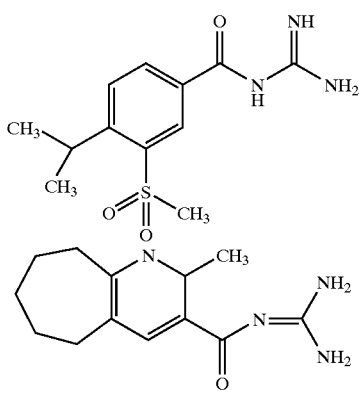

An agent which can be administered in combination with each Na—H inhibiting compound listed above is exemplified below and may be administered orally or parenterally (for example, nasally, via injection or suppository), and each may be incorporated into a single formulation or may individually be formulated together with a pharmaceutically acceptable carrier, excipient, binder or diluent and then administered separately or simultaneously. When an agent is formulated individually, such individually formulated agents may be mixed just before use for example using a diluent, or may be administered simultaneously or at a certain interval to an identical subject.

Examples of agents exhibiting synergistic effects when combined with Na—H inhibiting compounds:

Thrombolytic agent (for example, urokinase, alteplase);

Antiplatelet agent (for example, aspirin, ozagrel sodium, ticlopidine Hydrochloride);

Anticoagulant (for example, heparin, warfarin, argatroban);

Cardiotonic agent (for example, cathecolamine formulation such as dopamine hydrochloride and dobutamine hydrochloride or digitalis formulation such as digoxin);

Coronary dilator (nitrite formulation such as nitroglycerin, isosorbide nitrate and nicorandil, Ca antagonist such as nifedipine as well as dipyridamole);

Restenosis preventing agent (such as tranilast);

Hyperlipidemia treating agent (for example, clofibrate, probucol, cerivastatin Sodium);

Antiarrhythmic agent (for example, Class I antiarrhythmic agent such as disopyramide, lidocaine and procaineamide hydrochloride, Class III antiarrhythmic agent such as amiodarone hydrochloride and sotalol hydrochloride, β-blocker such as propranolol hydrochloride or Ca antagonist such as verapamil hydrochloride);

Hypotensive agent (for example, angiotensine converting enzyme inhibitor such as captopril, enalapril maleate and delapril, angiotensine receptor antagonist such as candesartan cilexetil and potassium losartan, diuretic such as furosemide and spironolactone, Ca antagonist such as amlodipine, manidipine hydrochloride and diltiazem hydrochloride, β-blocker such as atenolol and metoprol or α-blocker such as prazosin); and the like.

Since each of the novel optically active forms encompassed by Compound (I), namely, (S)-(−)-7-(5-fluoro-2-methylphenyl)-5-guanidinoimino-4-methyl-5,6,7,8-tetrahydroquinoline or a salt thereof as well as (S)-(−)-7-(2-chloro-5-fluorophenyl)-5-guanidinoimino-4-methyl-5,6,7,8-tetrahydroquinoline or a salt thereof has an excellent Na—H exchange inhibitory activity, low toxicity and high stability, it can be given as it is or in combination with an appropriate amount of a pharmaceutically acceptable carrier, excipient or diluent in the form of a pharmaceutical composition such as powder, granule, tablet, capsule (including soft capsule and microcapsule), liquid formulation, injection formulation and suppository safely via an oral or parenteral administration route, with a parenteral administration (including sublingual formulation) being preferred and a nasal preparation being beneficial particularly.

Such pharmaceutical composition exhibits an excellent Na—H exchange inhibitory activity which leads to a cell dysfunction improving effect and a cell protecting effect (especially on myocardial cell) in animals, especially in mammals (for example human, monkey, pig, dog, cat, rabbit, guinea pig, rat, mouse and the like), and thus is useful as a prophylactic or therapeutic agent for ischemic diseases (for example, myocardial infarction and accompanying dysfunctions, unstable angina and the like), restenosis after PTCA, arrhythmia, cardiac insufficiency, cardiac hypertrophy, hypertension and accompanying tissue failures, ischemic cerebral diseases (for example, cerebral disorders accompanying to cerebral infarction, cerebral hemorrhage, subarachnoid hemorrhage and the like) (preferably as a prophylactic or therapeutic agent against ischemic diseases such as myocardial infarction and accompanying dysfunctions, unstable angina and the like, restenosis after PTCA, arrhythmia, cardiac insufficiency, cardiac hypertrophy, more preferably as a prophylactic or therapeutic agent against ischemic diseases such as myocardial infarction, as a prophylactic or therapeutic agent against cardiac insufficiency). The concept of the prophylaxis of a cardiac insufficiency means here to include a treatment after a myocardial infarction, while the concept of the prophylaxis of a cardiac insufficiency means to include a prevention of the advancement or the exacerbation of the cardiac insufficiency.

Such pharmaceutical composition can be formulated in accordance with a method known per se, and the amount of (S)-(−)-7-(5-fluoro-2-methylphenyl)-5-guanidinoimino-4-methyl-5,6,7,8-tetrahydroquinoline or a salt thereof or (S)-(−)-7-(2-chloro-5-fluorophenyl)-5-guanidinoimino-4-methyl-5,6,7,8-tetrahydroquinoline or a salt thereof contained in the pharmaceutical composition is about 0.01 to about 20% (w/w).

A parenteral administration of the pharmaceutical composition according to the present invention includes subcutaneous, intravenous, intramuscular and intraperitoneal injections as well as drip infusions. An injectable preparation such as an aseptic aqueous or oily suspension for injection can be prepared using a suitable dispersing, wetting or suspending agent by a method known in the art. An aseptic injectable preparation may be an aseptic injectable solution or a suspension in a non-toxic parenterally-applicable diluent or a solvent such as an aqueous solution. A vehicle which can be employed or an acceptable solvent may for example be water, Ringer's solution and osmotic saline. In addition, an aseptic non-volatile oil can also be employed usually as a solvent or a suspending medium.

For this purpose, any non-volatile oil or fatty acid can be employed, including a naturally-occurring, synthetic or semi-synthetic fatty oil or fatty acid as well as a naturally-occurring, synthetic or semi-synthetic mono-, di- or triglyceride.

A suppository for a rectal administration of a pharmaceutical composition can be produced by mixing an active ingredient with a suitable non-irritating excipient, such as cacao butter or polyethylene glycol, which is a solid at ambient temperature but becomes a liquid at the temperature in the intestinal tract, and then is melted in the rectum to release the ingredient.

A solid dosage form for an oral administration of a pharmaceutical composition may for example be powder, granule, tablet, pill and capsule formulations as described above. In any of such dosage forms, an active ingredient may be mixed with at least one additive such as sucrose, lactose, celluloses, mannitol, maltitol, dextran, starch, agar, alginate, chitin, chitosan, pectin, tragacanth gum, gum arabic, gelatin, collagen, casein, albumin, synthetic or semi-synthetic polymer or glyceride. Such dosage form may further contain additional customary additives such as inert diluent, lubricant such as magnesium stearate, preservative such as paraben or sorbic acid, antioxidant such as ascorbic acid, α-tocopherol and cysteine, disintegrant, binder, thickening agent, buffering agent, sweetener, flavorant, perfume and the like. A tablet and a pill may further be covered with an enteric coating. An oral liquid formulation may also be a pharmaceutically acceptable emulsion, syrup, elixir, suspension or solution, which may contain an inert diluent employed usually in the art such as water.

While the dose of the pharmaceutical composition according to the present invention may vary depending on a particular subject, a route of the administration and a condition to be treated, a patient having a myocardial infarction (adult weighing about 60 kg) receives usually as a single dose about 0.005 to about 10 mg/kg, preferably about 0.01 to about 5 mg/kg, more preferably about 0.2 to about 1 mg/kg (about 0.3 to about 600 mg/adult, preferably about 0.6 to about 300 mg/adult, more preferably about 12 to about 60 mg/adult) as (S)-(−)-7-(5-fluoro-2-methylphenyl)-5-guanidinoimino-4-methyl-5,6,7,8-tetrahydroquinoline or a salt thereof or (S)-(−)-7-(2-chloro-5-fluorophenyl)-5-guanidinoimino-4-methyl-5,6,7,8-tetrahydroquinoline or a salt thereof, which is given preferably about one to about three times a day depending on the condition and the like. An acute onset of a disease, such as an acute state after the onset of a myocardial infarction, may be treated with a higher dose especially at a higher frequency, for example 4 times a day. Especially in the case of a patient having a myocardial infarction kept in an ICU, a daily intravenous dose of about 100 mg may be required.

DESCRIPTION OF THE PREFERRED EMBODIMENTS

The present invention is further described in Reference Examples, Examples, Formulation Examples and Experiments, which are not intended to restrict the invention. The room temperature in the specification means 0 to 25° C., and each symbol has a meaning described below.

mp: Melting point
s: Singlet
d: Doublet
t: Triplet
dd: Double doublet
ddd: Double double doublet
q: Quartet
m: Multiplet
br: Broad
$CDCl_3$: Heavy chloroform
$CD_3OD$: Heavy methanol
DMSO: Dimethyl sulfoxide
DCC: Dicyclohexyl carbodiimide
WSC: Water-soluble carbodiimide

EXAMPLE

Reference Example 1

2-Chlorobenzaldehyde (70.3 g) was added to a mixture of acetone (294 ml) and an aqueous solution (1.4 L) of sodium hydroxide (22.0 g) and the mixture was stirred at room temperature for 5 hours. An excessive acetone was distilled off under reduced pressure, and the residue was combined with ethyl acetate (1.4 L) and extracted. The ethyl acetate layer was washed with brine and dried (anhydrous magnesium sulfate), and then ethyl acetate was distilled off under reduced pressure to obtain a crude 2-chlorobenzalacetone (94.6 g) as a yellow oil. This oil was employed in the next step without a further purification. A 20% solution of sodium ethoxide in ethanol (170.1 g) was combined with diethyl malonate (80.1 g) at room temperature (resulting in instantaneous precipitation), and then with a solution of a crude 2-chlorobenzalacetone (94.6 g) in ethanol (40 ml). The reaction mixture was stirred with heating at 90° C. for 2 hours, allowed to stand to cool, and then cooled on ice (1 hour). The precipitate was recovered by a filtration, washed successively with ethyl acetate and isopropyl ether to obtain a crude 6-(2-chlorophenyl)-2-hydroxy-4-oxo-2-cyclohexenene-1-carboxylic acid ethyl ester monosodium salt (151.0 g) as a pale yellow powder. This powder was combined with 2M sodium hydroxide (350 ml) and stirred with heating at 100° C. for 2 hours. After allowing to stand to cool, 2.5 M sulfuric acid (350 ml) was added over a period of 15 minutes, and the mixture was stirred with heating at 100° C. for 2 hours. After allowing to stand to cool, ethyl acetate (1.4 L) was added and extracted. The ethyl acetate layer was washed with brine, dried (anhydrous magnesium sulfate), and then ethyl acetate was distilled off under reduced pressure. The precipitated crystal was washed successively with ethyl acetate-isopropyl ether (1:4) and isopropyl ether to obtain 5-(2-chlorophenyl)cyclohexane-1,3-dione (82.1 g) as a colorless crystal.

Mp. 157 to 158° C.

Reference Example 2

A mixture of 5-(2-chlorophenyl)-1,3-cyclohexanedione (1.1 g), 1-amino-2-butyne hydrochloride (0.5 g), molecular sieve 4A (2 g) and tetrahydrofuran (20 ml) was combined with triethylamine (0.48 g), stirred at room temperature for 1 hour, and then heated under reflux for 12 hours. After cooling, insolubles were filtered off, and the solvent was distilled off under reduced pressure. The residue was stirred at 220° C. for 4 hours. Ethyl acetate and aqueous sodium hydrogen carbonate were added, and the organic layer was washed successively with water and saturated brine, and then dried over anhydrous magnesium sulfate. After concentrating under reduced pressure, the residue was subjected to a column chromatography on a silica gel (EtOAc/hexane) to obtain a crystal which was then recrystallized from ethyl acetate-hexane to obtain 7-(2-chlorophenyl)-4-methyl-5,6,7,8-tetrahydroquinoline-5-one (0.20 g) as a colorless crystal.

Mp. 97 to 98° C.; $^1$H-NMR ($CDCl_3$) δ: 2.71 (3H, s), 2.84 (1H, dd, J=13, 16 Hz), 3.02 (1H, ddd, J=2, 4, 16 Hz), 3.30 (1H, dd, J=12, 17 Hz), 3.48 (1H, ddd, J=2, 4, 17 Hz), 3.88–4.07 (1H, m), 7.11 (1H, d, J=5 Hz), 7.16–7.34 (4H, m), 8.50 (1H, d, J=5 Hz).

Reference Example 3

A solution of 5-(2-chlorophenyl)cyclohexane-1,3-dione (2.5 g) and ammonium acetate (2.6 g) in ethanol (50 ml) was heated under reflux for 12 hours. The solvent was distilled off under reduced pressure, and aqueous sodium hydrogen carbonate was added and the mixture was extracted with ethyl acetate. The organic layer was washed with water and saturated brine, and dried over magnesium sulfate. The solvent was distilled off under reduced pressure, and the resultant crystal was recrystallized from ethyl acetate-hexane to obtain 1-amino-5-(2-chlorophenyl)cyclohexen-3-one (2.2 g) as a pale yellow crystal.

Mp. 199° C. (decomposition); $^1$H-NMR ($CDCl_3$) δ: 2.44–2.72 (4H, m), 3.77–3.97 (1H, m), 4.68 (2H, br), 5.35 (1H, s), 7.15–7.43 (4H, m).

Reference Example 4

A solution of 1-amino-5-(2-chlorophenyl)cyclohexen-3-one (2.7 g) in ethanol (50 ml) and toluene (150 m) was combined with acetyl acetoaldehyde dimethyl acetal (4.0 g) and 85% potassium hydroxide (0.67 g), and the mixture was heated under reflux. 85% Potassium hydroxide (0.14 g) was added three times at an interval of 30 minutes, and then heated under reflux further for 1 hour. The solvent was distilled off under reduced pressure, and the residue was combined with ethyl acetate, washed successively with water and saturated brine, and dried over magnesium sulfate. After concentrating under reduced pressure, the residue was subjected to a column chromatography on a silica gel (EtOAc-hexane) to obtain 7-(2-chlorophenyl)-4-methyl-5,6,7,8-tetrahydroquinolin-5-one (2.5 g) as a crystal. Melting point and NMR data were in agreement with those of the compound obtained in Reference Example 2.

Example 1 (Production of Compound A)

A mixture of 7-(2-chlorophenyl)-4-methyl-5,6,7,8-tetrahydroquinolein-5-one (0.20 g), aminoguanidine hydrochloride (0.085 g), concentrated hydrochloric acid (0.11 ml), water (0.11 ml) and ethanol (20 ml) was heated under reflux for 6 hours. The solvent was distilled off under reduced pressure, and the residue was dissolved in water, washed with ethyl acetate, and concentrated under reduced pressure. The residue was recrystallized from ethyl acetate-ethanol to obtain 7-(2-chlorophenyl)-5-guanidinoimino-4-methyl-5,6,7,8-tetrahydroquinoline hydrochloride (Compound A) (0.21 g) as a colorless crystal.

Mp. 204° C. (decomposition); Calculated as $C_{17}H_{18}N_5Cl.2HCl.0.8H_2O$: C, 49.18; H, 5.24; N, 16.87; Found C, 49.46; H. 5.10; N, 16.88; $^1$H-NMR (DMSO-$d_6$) δ: 2.65–3.00 (1H, m), 2.88 (3H, s), 3.15–3.78 (4H, m), 7.2–8.2 (4H, br), 7.28–7.53 (3H, m), 7.58–7.66 (1H, m), 7.83 (1H, d, J=6 Hz), 8.63 (1H, d, J=6 Hz), 11.45 (1H, s).

Example 2 (Production of Compound B)

(±)-7-(2-Chlorophenyl)-5-guanidinoimino-4-methyl-5,6,7,8-tetrahydroquinoline hydrochloride (123.9 g) was suspended in methanol (1200 ml) and treated dropwise with a 28% solution of sodium methoxide in methanol (119.2 ml). The mixture was stirred at 50° C. for 30 minutes. The solvent was distilled off under reduced pressure, and the residue was combined with water and then the crystal was recovered by a filtration. The crystal was washed with water and dried to obtain (±)-7-(2-chlorophenyl)-5-guanidinoimino-4-methyl-5,6,7,8-tetrahydroquinoline (109.3 g) as a colorless crystal. To a solution of (±)-7-(2-chlorophenyl)-5-guanidinoimino-4-methyl-5,6,7,8-tetrahydroquinoline (109.3 g) in isopropyl alcohol (700 ml), a solution of L-pyroglutamic acid (10 g) in isopropyl alcohol (150 m) was added dropwise at 50° C. over a period of 1.5 hours. The mixture was stirred at 50° C. for 1 hour and then at room temperature for 2 days. The crystal was recovered by a filtration and washed with isopropyl alcohol to obtain (−)-7-(2-chlorophenyl)-5-guanidinoimino-4-methyl-5,6,7,8-tetrahydroquinoline L-pyroglutamate (55.5 g, 88% ee). A recrystallization from ethanol resulted in an L-pyroglutamate (44.3 g, 97% ee). The crystal of the salt thus obtained was suspended in methanol (500 ml) and combined with a 28% methanol solution of sodium methoxide (10.9 ml). The mixture was stirred at 50° C. for 30 minutes and then the solvent was distilled off under reduced pressure. The crystal obtained was washed with water and dried to obtain (−)-7-(2-chlorophenyl)-5-guanidinoimino-4-methyl-5,6,7,8-tetrahydroquinoline (38.9 g). (This compound was proven to have an absolute configuration of an S form based in an X-ray crystal structure analysis.)

The product thus obtained was dissolved in ethanol (400 ml) and combined with methanesulfonic acid (21.1 g). The solvent was distilled off under reduced pressure and the resultant crystal was recrystallized from ethanol to obtain (−)-7-(2-chlorophenyl)-5-guanidinoimino-4-methyl-5,6,7,8-tetrahydroquinoline methanesulfonate (Compound B) (46.8 g, 99.2% ee).

Mp. 194 to 195° C.; $[\alpha]_D$ −56.9° (c=1, MeOH); Calculated as $C_{17}H_{18}N_5Cl.2MeSO_3H$: C, 43.88; H, 5.04; N, 13.47; Cl, 6.82; Found C, 43.67; H, 4.90; N, 13.18; Cl, 6.76; $^1$H-NMR (DMSO-$d_6$) δ: 2.40 (6H, s), 2.78 (1H, dd, J=12, 18 Hz), 2.89 (3H, s), 3.08–3.32 (2H, m), 3.44–3.80 (2H, m), 7.2–8.1 (4H, br), 7.31–7.56 (3H, m), 7.58–7.66 (1H, m), 7.86 (1H, d, J=6 Hz), 8.66 (1H, d, J=6 Hz), 10.77 (1H, s).

Reference Example 5

A solution of 2-bromo-4-fluorotoluene (16.0 g) in anhydrous tetrahydrofuran was treated dropwise at −78° C. with a 1.6 M solution of butyllithium in hexane (55.5 ml). At the same temperature, the mixture was stirred and treated dropwise with a solution of dimethylformamide (6.8 g) in tetrahydrofuran (20 ml). After being allowed to warm to 0° C., the reaction mixture was combined with ice-water. The reaction mixture was extracted with ethyl acetate, and the organic layer was washed successively with water and saturated brine, and then dried over magnesium sulfate. The solvent was distilled off under reduced pressure to obtain 5-fluoro-2-methylbenzaldehyde (11.5 g) as an oil.

A mixture of acetone (80 ml), sodium hydroxide (3.7 g) and water (100 ml) was treated at room temperature dropwise with a solution of 5-fluoro-2-methylbenzaldehyde (11.5 g) in acetone (30 ml) and stirred at the same temperature for 1 hour. Acetone was distilled off under reduced pressure, and the mixture was extracted with ethyl acetate. The organic layer was washed successively with water and saturated brine and concentrated under reduced pressure to obtain 4-(5-fluoro-2-methylphenyl)-3-buten-2-one (13.4 g).

A 20% solution of sodium ethoxide in ethanol (29.7 g) was combined at 0C with diethyl malonate (14.0 g) and then with 4-(5-fluoro-2-methylphenyl)-3-buten-2-one (13.4 g) in portions. The reaction mixture was stirred at room temperature for 30 minutes, and then stirred with heating for 2 hours. After allowing to stand to cool, the solvent was distilled off, and the residue was combined with water and the aqueous layer was washed with ethyl acetate and then concentrated. 2M Sodium hydroxide (46 ml) was added and the mixture was heated under reflux for 1 hour. After allowing to stand to cool, 2.5M sulfuric acid (46 ml) was added over 10 minutes, and the mixture was heated under reflux for 30 minutes. After allowing to stand to cool, the precipitated crystal was recovered by a filtration and washed successively with water and isopropyl ether to obtain 5-(5-fluoro-2-methylphenyl)cyclohexane-1,3-dione (8.6 g) as a colorless crystal.

Mp. 175 to 176° C.; $^1$H-NMR (CDCl$_3$) δ: 2.30 (3H, s), 2.27–2.56 (4H, m), 2.5–4.3 (1H, br), 3.44–3.63 (1H, m), 5.55 (1H, s), 6.77–7.01 (2H, m), 7.09–7.17 (1H, m).

Reference Example 6

A solution of 5-(5-fluoro-2-methylphenyl)cyclohexane-1,3-dione (3.0 g) and ammonium acetate (3.1 g) in ethanol (50 ml) was heated under reflux for 14 hours. The solvent was distilled off under reduced pressure, and the residue was dissolved in ethyl acetate, washed successively with water and saturated brine and then dried over magnesium sulfate. The solvent was distilled off under reduced pressure to obtain 1-amino-5-(5-fluoro-2-methylphenyl)cyclohexen-3-one. This was dissolved in ethanol (70 ml) and toluene (120 ml), combined with 3-oxobutylaldehyde dimethyl acetal (4.1 g) and potassium hydroxide powder (0.57 g), and then heated under reflux. The mixture was combined with potassium hydroxide powder (0.12 g) after 30 minutes and with potassium hydroxide powder (0.12 g) and 3-oxobutylaldehyde dimethylacetal (0.33 g) after 1 hour and further with potassium hydroxide powder (0.12 g) after 1 hour and 30 minutes, and then stirred at the same temperature for 2 hours. After cooling, the solvent was distilled off under reduced pressure, and ethyl acetate was added. The organic layer was washed successively with water and saturated brine, and dried over magnesium sulfate. Ethyl acetate was distilled off under reduced pressure, and the residue was subjected to a silica gel column (ethyl acetate-hexane) to obtain a crystal which was then recrystallized from ethyl acetate-hexane to obtain 7-(5-fluoro-2-methylphenyl)-4-methyl-5,6,7,8-tetrahydroquinolin-5-one (1.5 g).

Mp. 113 to 114° C.; $^1$H-NMR (CDCl$_3$) δ: 2.33 (3H, s), 2.71 (3H, s), 2.78–2.98 (2H, m), 3.24 (1H, dd, J=11, 16 Hz), 3.28–3.44 (1H, m), 3.55–3.74 (1H, m), 6.82–7.04 (2H, m), 7.12 (1H, d, J=5 Hz), 7.07–7.22 (2H, m), 8.50 (1H, d, J=5 Hz).

Example 3 (Production of Compound C)

A solution of 7-(5-fluoro-2-methylphenyl)-4-methyl-5,6,7,8-tetrahydroquinolin-5-one (1.1 g) and aminoguanidine hydrochloride (0.54 g) in ethanol (30 ml) was combined with concentrated hydrochloric acid (1.0 ml) and water (1.0 ml) and heated under reflux for 6 hours. The solvent was distilled off under reduced pressure, and the residue was dissolved in water and washed with ethyl acetate. The aqueous layer was made alkaline with aqueous sodium hydrogen carbonate and extracted with ethyl acetate. The organic layer was washed successively with water and saturated brine, dried over magnesium sulfate and concentrated under reduced pressure. The residue was dissolved in ethanol, combined with 1N hydrochloric acid (10 ml) and concentrated, and then the precipitated crystal was recrystallized from ethanol to obtain 7-(5-fluoro-2-methylphenyl)-5-guanidinoimino-4-methyl-5,6,7,8-tetrahydroquinoline hydrochloride (Compound C) (1.4 g) as a colorless crystal.

Mp. 202 to 205° C.; Calculated as C$_{18}$H$_{20}$N$_5$F.2HCl.0.5H$_2$O: C, 53.08; H, 5.69; N, 17.19; Found C, 53.33; H, 5.87; N, 16.94; $^1$H-NMR (DMSO-d$_6$) δ: 2.31 (3H, s), 2.72–3.03 (1H, m), 2.90 (3H, s), 3.13–3.57 (4H, m), 6.93–7.06 (1H, m), 7.17–7.4 (2H, m), 7.5–8.4 (4H, br), 7.85 (1H, d, J=6 Hz), 8.65 (1H, d, J=6 Hz), 11.39 (1H, s).

Example 4 (Production of Compounds D, E and F)

(±)-7-(5-Fluoro-2-methylphenyl)-5-guanidinoimino-4-methyl-5,6,7,8-tetrahydroquinoline hydrochloride (43.8 g) was suspended in methanol (300 ml), and treated dropwise with a 28% solution of sodium methoxide in methanol (53.1 g). The mixture was concentrated under reduced pressure, and the residue was washed with water and dried to obtain (±)-7-(5-fluoro-2-methylphenyl)-5-guanidinoimino-4-methyl-5,6,7,8-tetrahydroquinoline (33.0 g).

A solution of (±)-7-(5-Fluoro-2-methylphenyl)-5-guanidinoimino-4-methyl-5,6,7,8-tetrahydroquinoline (2.0 g) in ethanol (25 ml) was combined with D-pyroglutamic acid (0.79 g) at 80° C. to form a uniform solution. The solution was allowed to warm to room temperature gradually, and then stirred at the same temperature for 14 hours. The precipitated crystal was recovered by a filtration and recrystallized from ethanol to obtain (−)-7-(5-fluoro-2-methylphenyl)-5-guanidinoimino-4-methyl-5,6,7,8-tetrahydroquinoline D-pyrglutamate (1.2 g). This crystal was suspended in methanol (20 ml) and combined with a 28% solution of sodium methoxide in methanol (0.24 g), and then the solvent was distilled off under reduced pressure. The resultant crystal was washed with water and dried to obtain a free form (0.43 g). This was dissolved in ethanol (15 ml) and combined with methanesulfonic acid (0.24 g). The solvent was distilled off under reduced pressure and the resultant crystal was recrystallized from ethanol to obtain (−)-7-(5-fluoro-2-methylphenyl)-5-guanidinoimino-4-methyl-5,6,7,8-tetrahydroquinoline methanesulfonate (Compound D) (0.5 g, 99.7% ee).

Mp. 202 to 204° C. $[α]_D$ −61.4° (c=1, MeOH); Calculated as C$_{18}$H$_{20}$FN$_5$.2MeSO$_3$H: C, 46.41; H, 5.45; N, 13.51; Found C, 46.28; H, 5.30; N, 13.51; $^1$H-NMR (DMSO-d$_6$) δ: 2.30 (3H, s), 2.35 (6H, s), 2.62–2.95 (1H, m), 2.86 (3H, s), 2.99–3.24 (2H, m), 3.3–3.6 (2H, m), 6.96–7.11 (1H, m), 7.19–7.42 (2H, m), 7.7 (4H, br), 7.81 (1H, d, J=5 Hz), 8.65 (1H, d, J=5 Hz), 10.68 (1H, s).

A solution of (−)-7-(5-fluoro-2-methylphenyl)-5-guanidinoimino-4-methyl-5,6,7,8-tetrahydroquinoline (1.5 g) in ethanol (20 ml) was combined with concentrated hydrochloric acid (1.2 ml) and concentrated. The resultant crystal was recrystallized from a solvent mixture of ethanol and water to obtain (−)-7-(5-fluoro-2-methylphenyl)-5-guanidinoimino-4-methyl-5,6,7,8-tetrahydroquinoline hydrochloride (Compound E) (0.96 g, 99.3% ee). (This compound was proven to have an absolute configuration of an S form based in an X-ray crystal structure analysis.)

Mp. 192 to 198° C.; Calculated as C$_{18}$H$_{20}$FN$_5$.2HCl1H$_2$O: C, 51.93; H, 5.81; N, 16.82; Found C, 51.94; H, 5.84; N, 16.74; $^1$H-NMR (DMSO-d$_6$) δ: 2.31 (3H, s), 2.66–3.03 (1H, m), 2.89 (3H, s), 3.12–3.6 (4H, m), 6.94–7.06 (1H, m), 7.16–7.37 (2H, m), 7.4–8.3 (4H, br) 7.85 (1H, d, J=6 Hz), 8.64 (1H, d, J=6 Hz), 11.41 (1H, s).

A mother liquor and washings which had been resolved with D-pyroglutamic acid were combined with a 28% solution of sodium methoxide in methanol (0.22 g), concentrated and washed with water to obtain a (+)-isomer-rich crystal (1.1 g). This was dissolved in ethanol (10 ml) and combined with L-pyroglutamic acid (0.42 g) at 80° C. to form a uniform solution. The solution was allowed to warm to room temperature gradually, and the mixture was stirred at room temperature for 14 hours. The precipitated crystal was recovered by a filtration, washed with ethanol to obtain (+)-7-(5-fluoro-2-methylphenyl)-5-guanidinoimino-4-methyl-5,6,7,8-tetrahydroquinoline L-pyroglutamate (1.1 g). This crystal was suspended in methanol (15 ml) and combined with a 28% solution of sodium methoxide in methanol (0.47 g) and the solvent was distilled off under reduced pressure. The residue was washed with water and dried to obtain a free form (0.77 g). This was dissolved in ethanol (20 ml) and combined with methanesulfonic acid (0.47 g). The solvent was distilled off under reduced pressure and the resultant crystal was recrystallized from ethanol to obtain (+)-7-(5-fluoro-2-methylphenyl)-5-guanidinoimino-4-methyl-5,6,7,8-tetrahydroquinoline methanesulfonate (Compound F) (1.1 g, 99.4% ee).

Mp. 202 to 204° C.; $[α]_D$ +60.5° (c=1, MeOH); Calculated as C$_{18}$H$_{20}$FN$_5$.2MeSO$_3$H: C, 46.41; H, 5.45; N, 13.51; Found C, 46.27; H, 5.30; N, 13.48; $^1$H-NMR (DMSO-d$_6$) was in agreement with that of Compound D.

Example 5 (Production of Compound G)

A solution of 2-chloro-5-fluorotoluene (5.0 g) in acetic anhydride (40 ml) was treated dropwise with concentrated sulfuric acid (40 ml) with cooling on ice. Subsequently, a solution of chromic anhydride (9.3 g) in acetic anhydride (40 ml) was added dropwise over a period of 2 hours. At the same temperature, the mixture was stirred for 1 hour, and added to an ice-water. The mixture was extracted with diethyl ether and the organic layer was washed successively with aqueous sodium carbonate, water and saturated brine, and then dried over magnesium sulfate. The solvent was distilled off under reduced pressure, and the residue was dissolved in tetrahydrofuran (10 ml), combined with water (4 ml) and concentrated sulfuric acid (4 ml), and heated with stirring at 100° C. for 30 minutes. After allowed to stand to cool, the reaction mixture was extracted with ethyl acetate, and the organic layer was washed successively with aqueous sodium carbonate, water and saturated brine, and dried over magnesium sulfate. The solvent was distilled off and the residue was subjected to a column chromatography on a silica gel to obtain 2-chloro-5-fluorobenzaldehyde (1.6 g).

The same reaction was repeated to obtain 2-chloro-5-fluorobenzaldehyde (1.2 g).

Sodium hydroxide (0.78 g) was dissolved in water (55 ml) and treated dropwise with acetone (55 ml) followed by a solution of 2-chloro-5-fluorobenzaldehyde (2.8 g) in acetone (10 ml). The reaction mixture was stirred at room temperature for 2 hours. Acetone was distilled off under reduced pressure, and the residue was extracted with ethyl acetate. The organic layer was washed successively with water and saturated brine, and concentrated under reduced 5 pressure to obtain 4-(2-chloro-5-fluorophenyl)-3-buten-2-one (0.24 g).

A 20% solution of sodium ethoxide in ethanol (0.43 g) was combined at room temperature with diethyl malonate (0.2 g) followed by 4-(2-chloro-5-fluorophenyl)-3-buten-2-one (0.24 g) in portions at 0C. The reaction mixture was stirred at room temperature for 30 minutes and heated under reflux for 2 hours. After allowing to stand to cool, the solvent was distilled off, and the residue was dissolved in water and the aqueous layer was washed with ethyl acetate and concentrated. 2M sodium hydroxide (0.7 ml) was added and the mixture was heated under reflux for 2 hours. After allowing to stand to cool, 2.5 M sulfuric acid (0.7 ml) was added, and the mixture was heated under reflux for 15 minutes. The mixture was extracted with ethyl acetate, and the organic layer was washed successively with water and saturated brine. After drying over magnesium sulfate followed by distilling the solvent off under reduced pressure, 5-(2-chloro-5-fluorophenyl)cyclohexane-1,3-dione (0.17 g) as an oil.

A solution of 5-(2-chloro-5-fluorophenyl)cyclohexane-1,3-dione (0.17 g) and ammonium acetate (0.16 g) in ethanol (10 ml) was heated under reflux for 12 hours. The solvent was distilled off under reduced pressure, and the residue was combined with ethyl acetate and then the organic layer was washed successively with aqueous sodium carbonate, water and saturated brine and dried over magnesium sulfate. The solvent was distilled off under reduced pressure, and the residue was dissolved in ethanol (3.5 ml) and toluene (6 ml), combined with 3-oxobutylaldehyde dimethyl acetal (0.21 g) and potassium hydroxide powder (34 mg) and then heated under reflux. The mixture was combined with potassium hydroxide powder (7 mg) after 30 minutes and with potassium hydroxide powder (7 mg) and 3-oxobutylaldehyde dimethyl acetal (17 mg) after 1 hour and further with potassium hydroxide powder (7 mg) after 1 hour and 30 minutes, and then stirred at the same temperature for 2 hours. After cooling, the solvent was distilled off under reduced pressure, and then the mixture was extracted with ethyl acetate. The organic layer was washed successively with water and saturated brine, and dried over magnesium sulfate. Ethyl acetate was distilled off under reduced pressure, and the residue was subjected to a column chromatography on a silica gel (ethyl acetate-hexane) to obtain 7-(2-chloro-5-fluorophenyl)-4-methyl-5,6,7,8-tetrahydroquinolin-5-one.

A solution of 7-(2-chloro-5-fluorophenyl)-4-methyl-5,6,7,8-tetrahydroquinolin-5-one in ethanol (10 ml) was combined with aminoguanidine hydrochloride (0.041 g), concentrated hydrochloric acid (0.078 ml) and water (0.078 ml), and the mixture was heated under reflux for 4 hours. The solvent was distilled off under reduced pressure, and the residue was combined with water and the aqueous layer was washed with ethyl acetate. The aqueous layer was made alkaline with aqueous sodium hydrogen carbonate and extracted with ethyl acetate. The organic layer was washed successively with water and saturated brine, dried over magnesium sulfate and concentrated under reduced pressure. The residue was dissolved in 1N hydrochloric acid (1 ml) and concentrated. The resultant crystal was recrystallized from ethanol-ethyl acetate to obtain 7-(2-chloro-5-fluorophenyl)-5-guanidinoimino-4-methyl-5,6,7,8-tetrahydroquinoline hydrochloride (Compound G) (0.05 g) as a colorless crystal.

Mp. 268° C. (decomposition); $^1$H-NMR (DMSO-$d_6$) δ: 2.76–3.05 (1H, m), 2.84 (3H, s), 3.13–3.75 (4H, m), 7.0–8.4 (4H, br), 7.2–7.34 (1H, m), 7.52–7.66 (2H, m), 7.76 (1H, d, J=6 Hz), 8.6 (1H, d, J=6 Hz), 11.36 (1H, s).

Example 6 (Production of Compound H, I and J)

(±)-7-(2-chloro-5-fluorophenyl)-5-guanidinoimino-4-methyl-5,6,7,8-tetrahydroquinoline hydrochloride (8.8 g) was suspended in methanol (100 ml) and treated dropwise with a 28% solution of sodium methoxide in methanol (8.9 g) The mixture was concentrated under reduced pressure, and the result was washed with water and dried to obtain (±)-7-(2-chloro-5-fluorophenyl)-5-guanidinoimino-4-methyl-5,6,7,8-tetrahydroquinoline (7.1 g).

A solution of (±)-7-(2-chloro-5-fluorophenyl)-5-guanidinoimino-4-methyl-5,6,7,8-tetrahydroquinoline (7.1 g) in ethanol (85 ml) was combined with L-pyroglutamic acid (2.72 g) and heated to form a uniform solution. The mixture was allowed to stand to cool gradually, and stirred at room temperature for 14 hours. The crystal precipitated was recovered by a filtration and washed with ethanol to obtain (+)-7-(2-chloro-5-fluorophenyl)-5-guanidinoimino-4-methyl-5,6,7,8-tetrahydroquinoline L-pyroglutamate (4.1 g). This crystal was suspended in methanol (50 ml) and combined with a 28% solution of sodium methoxide in methanol (1.7 g) and then the solvent was distilled off under reduced pressure. The resultant crystal was washed with water and dried to obtain a crystal (3.1 g). This was dissolved in ethanol (20 ml) and combined with methanesulfonic acid (1.8 g). The solvent was distilled off under reduced pressure, and the resultant crystal was recrystallized from ethanol to obtain (+)-7-(2-chloro-5-fluorophenyl)-5-guanidinoimino-4-methyl-5,6,7,8-tetrahydroquinoline methanesulfonate (Compound H)(3.6 g, 99.3% ee).

Mp. 209 to 212° C.; $[\alpha]_D$+57.2° (c=1, MeOH); Calculated as $C_{17}H_{17}ClFN_5 \cdot 2MeSO_3H$: C, 42.42; H, 4.68; N, 13.02; Found C, 42.43; H, 4.68; N, 13.13; $^1$H-NMR (DMSO-$d_6$) δ:

2.43 (6H, s), 2.73–2.92 (1H, m), 2.90 (3H, s), 3.06–3.31 (2H, m), 3.37–3.79 (2H, m), 7.0–8.6 (4H, br), 7.14–7.26 (1H, m), 7.48–7.62 (2H, m), 7.85 (1H, d, J=6 Hz), 8.68 (1H, d, J=6 Hz), 10.86 (1H, s).

A mother liquor and washings which had been resolved with L-pyroglutamic acid were combined with a 28% solution of sodium methoxide in methanol (2.6 g), concentrated and washed with water to obtain a (−)-isomer-rich crystal (3.7 g). This was dissolved in ethanol (30 ml) and combined with a solution of D-pyroglutamic acid (1.4 g) in ethanol (10 ml) at 80° C. The solution was allowed to warm to room temperature gradually, and the mixture was stirred at room temperature for 14 hours. The precipitated crystal was recovered by a filtration, washed with ethanol to obtain (−)-7-(2-chloro-5-fluorophenyl)-5-guanidinoimino-4-methyl-5,6,7,8-tetrahydroquinoline D-pyroglutamate (4.0 g). This crystal was suspended in methanol (40 ml) and combined with a 28% solution of sodium methoxide in methanol (1.6 g) and the solvent was distilled off under reduced pressure. The residue was washed with water and dried to obtain (−)-7-(2-chloro-5-fluorophenyl)-5-guanidinoimino-4-methyl-5,6,7,8-tetrahydroquinoline (2.9 g). (−)-7-(2-Chloro-5-fluorophenyl)-5-guanidinoimino-4-methyl-5,6,7,8-tetrahydroquinoline (1.7 g) was dissolved in ethanol (30 ml) and combined with methanesulfonic acid (0.97 g). The solvent was distilled off under reduced pressure and the resultant crystal was recrystallized from ethanol to obtain (−)-7-(2-chloro-5-fluorophenyl)-5-guanidinoimino-4-methyl-5,6,7,8-tetrahydroquinoline methanesulfonate (Compound I) (2.3 g, 99.5% ee).

Mp. 206 to 209° C.; $[\alpha]_D$ −58.2° (c=1, MeOH); Calculated as $C_{17}H_{17}ClFN_5 \cdot 2MeSO_3H$: C, 42.42; H, 4.68; N, 13.02; Found C, 42.34; H, 4.67; N, 13.06; $^1$H-NMR (DMSO-$d_6$) was in agreement with that of Compound H.

A solution of (−)-7-(2-chloro-5-fluorophenyl)-5-guanidinoimino-4-methyl-5,6,7,8-tetrahydroquinoline (1.2 g) in ethanol (20 ml) was combined with concentrated hydrochloric acid (0.76 ml) and concentrated. The resultant crystal was recrystallized from a solvent mixture of ethanol and water to obtain (−)-7-(2-chloro-5-fluorophenyl)-5-guanidinoimino-4-methyl-5,6,7,8-tetrahydroquinoline hydrochloride (Compound J) (1.3 g, 99.4% ee). (This compound was proven to have an absolute configuration of an S form based in an X-ray crystal structure analysis.)

Mp. 194 to 197° C.; $[\alpha]_D$ −71.2° (c=1, MeOH); Calculated as $C_{18}H_{20}FN_5 \cdot 2HCl \cdot 0.5H_2O$: C, 47.74; H, 4.71; N, 16.37; Found C, 47.56; H, 4.97; N, 16.56; $^1$H-NMR (DMSO-$d_6$) δ: 2.75–3.02 (1H, m), 2.90 (3H, s), 3.15–3.32 (1H, m), 3.36–3.83 (2H, m), 6.13–7.28 (1H, m), 7.48–7.60 (2H, m), 7.92 (4H, br), 7.85 (1H, d, J=6 Hz), 8.65 (1H, d, J=6 Hz), 11.53 (1H, s).

Reference Example 7

A mixture of acetone (45 ml), sodium hydroxide (3.1 g) and water (230 ml) was combined at room temperature with a solution of 2,5-difluorobenzaldehyde (10.0 g) in acetone (10 ml) and stirred at the same temperature for 30 minutes. Acetone was distilled off under reduced pressure and extracted with ethyl acetate. The organic layer was washed successively with water and saturated brine and concentrated under reduced pressure to obtain 4-(2,5-difluorophenyl)-3-buten-2-one (13.8 g).

A 20% solution of sodium ethoxide in ethanol (27.7 g) was combined at room temperature with diethyl malonate (13.0 g) and then with 4-(2,5-difluorophenyl)-3-buten-2-one (13.8 g) in portions. The reaction mixture was stirred at room temperature for 30 minutes and then heated with stirring for 2 hours. After allowing to stand to cool, the solvent was distilled off, and the residue was combined with water, and the aqueous layer was washed with ethyl acetate and concentrated. 2N Sodium hydroxide (42 ml) was added and the mixture was heated under reflux for 2 hours. After allowing to stand to cool, 2.5 M sulfuric acid (42 ml) was added over a period of 10 minutes, and then the mixture was heated under reflux for 3 hours. After allowing to stand to cool, the precipitated crystal was recovered by a filtration and washed successively with water and isopropyl ether to obtain 5-(2,5-difluorophenyl)cyclohexane-1,3-dione (11.6 g) as a colorless crystal.

Mp. 176° C. (decomposition); $^1$H-NMR (DMSO-$d_6$) δ: 2.0–3.0 (4H, m), 3.43–3.64 (1H, m), 5.31 (1H, s), 7.04–7.37 (4H, m), 11.26 (1H, br).

Reference Example 8

A solution of 5-(2,5-difluorophenyl)cyclohexane-1,3-dione (4.0 g) and ammonium acetate (4.1 g) in ethanol (60 ml) was heated under reflux for 12 hours. The reaction mixture was concentrated under reduced pressure, and the residue was washed with water and dried to obtain 1-amino-5-(2,5-difluorophenyl)cyclohexan-3-one (3.7 g).

A mixture of 1-amino-5-(2,5-difluorophenyl)cyclohexan-3-one (3.7 g), 3-oxobutylaldehyde dimethyl acetal (5.5 g), toluene (120 ml) and ethanol (70 ml) was stirred at 115° C. with adding potassium hydroxide powder (0.77 g). The mixture was combined with potassium hydroxide powder (0.16 g) after 30 minutes and with potassium hydroxide powder (0.16 g) and 3-oxobutylaldehyde dimethyl acetal (0.44 g) after 1 hour and further with potassium hydroxide powder (0.16 g) after 1 hour and 30 minutes, and then stirred at the same temperature for 5 hours. After cooling, the solvent was distilled off under reduced pressure and ethyl acetate was added. The organic layer was washed successively with water and saturated brine, and dried over magnesium sulfate. Ethyl acetate was distilled off under reduced pressure, and the residue was subjected to a silica gel column (ethyl acetate-hexane), and the resultant crystal was recrystallized from ethyl acetate-hexane to obtain 7-(2,5-difluorophenyl)-4-methyl-5,6,7,8-tetrahydroquinolin-5-one (2.3 g).

Mp. 75 to 76° C.; $^1$H-NMR (CDCl$_3$) δ: 2.70 (3H, s), 2.86 (1H, dd, J=12, 16 Hz), 2.99 (1H, ddd, J=2, 5, 16 Hz), 3.33 (1H, dd, J=11, 17 Hz), 3.37–3.53 (1H, m), 3.66–3.89 (1H, m), 6.88–7.24 (3H, m), 7.11 (1H, d, J=5 Hz), 8.50 (1H, d, J=5 Hz).

Example 7 (Production of Compound K)

A solution of 7-(2,5-difluorophenyl)-4-methyl-5,6,7,8-tetrahydroquinolin-5-one (1.2 g) and aminoguanidine hydrochloride (0.58 g) in ethanol (30 ml) was combined with concentrated hydrochloric acid (1.1 ml) and water (1.1 ml), and the mixture was heated under reflux for 14 hours. The solvent was distilled off under reduced pressure, and the resultant crystal was recrystallized from ethanol to obtain 7-(2,5-difluorophenyl)-5-guanidinoimino-4-methyl-5,6,7,8-tetrahydroquinoline hydrochloride (Compound K) (1.6 g) as a colorless crystal.

mp. 290° C. (decomposition); $^1$H-NMR (DMSO-$d_6$) δ: 2.6–3.03 (1H, m), 2.87 (3H, s), 3.14–3.72 (4H, m), 7.12–7.38 (2H, m), 7.42–7.56 (1H, m), 7.6–8.4 (4H, br), 7.83 (1H, d, J=6 Hz), 8.64 (1H, d, J=6 Hz), 11.58 (1H, s).

Reference Example 9

A mixture of 5-(5-fluoro-2-methylphenyl)-cyclohexane-1,3-dione (1.5 g) and ammonium acetate (1.6 g) in butanol (30 ml) was combined with acetylacetone (2.0 g) and heated under reflux for 3 days. The solvent was distilled off under reduced pressure, and the residue was dissolved in ethyl acetate, washed successively with aqueous sodium hydrogen carbonate, water and saturated brine, and dried over magnesium sulfate. The mixture was concentrated under reduced pressure, and the residue was subjected to a column chromatography on a silica gel (ethyl acetate-hexane) to obtain 7-(5-fluoro-2-methylphenyl)-2,4-dimethyl-5,6,7,8-tetrahydroquinolin-5-one (1.2 g) as an oil.

$^1$H-NMR (CDCl$_3$) δ: 2.32 (3H, s), 2.54 (3H, s), 2.67 (3H, s), 2.75–3.0 (2H, m), 3.12–3.43 (H, m), 3.54–3.78 (1H, m), 6.92 (1H, s), 6.82–7.09 (3H, m), 7.10–7.23 (1H, m).

Example 8 (Production of Compound L)

A solution of 7-(5-fluoro-2-methylphenyl)-2,4-dimethyl-5,6,7,8-tetrahydroquinolin-5-one (1.1 g) and aminoguanidine hydrochloride (0.52 g) in ethanol (30 ml) was combined with concentrated hydrochloric acid (1.0 ml) and water (1.0 ml), and the mixture was heated under reflux for 12 hours. The mixture was concentrated under reduced pressure, and the residue was recrystallized from ethanol to obtain 7-(5-fluoro-2-methylphenyl)-5-guanidinoimino-2,4-dimethyl-5,6,7,8-tetrahydroquinoline hydrochloride (Compound L) (1.25 g) as a colorless crystal.

Mp. 201 to 203° C.; $^1$H-NMR (DMSO-d$_6$) δ: 2.3 (3H, s), 2.6–3.0 (1H, m), 2.72 (3H, s), 2.83 (3H, s), 3.0–4.0 (4H, m), 6.97–7.12 (1H, m), 7.18–7.45 (2H, m), 7.5–8.4 (4H, br), 7.72 (1H, s), 11.32 (1H, s).

Formulation Example 1

70 mg of Compound B synthesized in Example 2 was dissolved in 7 ml of distilled water. 0.5 ml of this solution was added to 195 mg of calcium carbonate (mean particle size: 38 μm) and combined further with 0.5 ml of distilled water, and freeze-dried to obtain a powder, which was then mixed in a mortar to obtain a pharmaceutical preparation.

Formulation Example 2

33 mg of Compound B synthesized in Example 2 was dissolved in 3.3 ml of distilled water. 1 ml of this solution was added to 190 mg of calcium carbonate (mean particle size: 38 μm) and freeze-dried to obtain a powder, which was then mixed in a mortar to obtain a pharmaceutical preparation.

Formulation Example 3

33 mg of Compound B synthesized in Example 2 was dissolved in 3.3 ml of distilled water. 2 ml of this solution was added to 180 mg of calcium carbonate (mean particle size: 38 μm) and freeze-dried to obtain a powder, which was then mixed in a mortar to obtain a pharmaceutical preparation.

Formulation Example 4

70 mg of Compound B synthesized in Example 2 was dissolved in 7 ml of distilled water. 6 ml of this solution was added to 240 mg of calcium carbonate (mean particle size: 38 μm) and freeze-dried to obtain a powder, which was then mixed in a mortar to obtain a pharmaceutical preparation.

Formulation Example 5

12.5 mg of Compound B synthesized in Example 2 was dissolved in 0.5 ml of a 5% aqueous solution of mannitol to obtain a pharmaceutical preparation in the form of a solution.

Formulation Example 6

25 mg of Compound B synthesized in Example 2 was dissolved in 0.5 ml of a 5% aqueous solution of mannitol to obtain a pharmaceutical preparation in the form of a solution.

Formulation Example 7

30 mg of Compound B synthesized in Example 2 was dissolved in 3 ml of distilled water. 2 ml of this solution was added to 180 mg of hydroxyapatite (TAIHEIKAGAKU SANGYO, HAP100) and freeze-dried to obtain a powder, which was then mixed in a mortar to obtain a pharmaceutical preparation.

Formulation Example 8

30 mg of Compound B synthesized in Example 2 was dissolved in 3 ml of distilled water. 2 ml of this solution was added to 180 mg of crystalline cellulose (ASAHI KASEI KOGYO, AVICEL) and freeze-dried to obtain a powder, which was then mixed in a mortar to obtain a pharmaceutical preparation.

Formulation Example 9

30 mg of Compound B synthesized in Example 2 was dissolved in 3 ml of distilled water. 2 ml of this solution was added to 180 mg of hydroxypropyl cellulose (NIPPON SODA) and freeze-dried to obtain a powder, which was then mixed in a mortar to obtain a pharmaceutical preparation.

Comparative 1

9 mg of Compound B synthesized in Example 2 was dissolved in 4.5 ml of a 5% aqueous solution of mannitol to obtain a pharmaceutical preparation in the form of a solution.

Experiment 1

(Method)

A male SD rat (8 weeks old) was anesthetized with ether and each of the preparations of Formulation Examples 1 to 6 was given into the left nasal cavity. The dose of Compound B was 0.75 mg/kg (Formulation Example 1), 1.5 mg/kg (Formulation Example 2), 3.0 mg/kg (Formulation Example 3), 6.0 mg/kg (Formulation Example 4), 1.5 mg/kg (Formulation Example 5) and 3.0 mg/kg (Formulation Example 6). Each of the preparations of Formulation Examples 1 to 4 was taken as a portion of about 10 mg, which was filled in a polyethylene tube (INTRAMEDIC PE90, BECKTON DICKINSON) and the polyethylene tube was inserted into the nasal cavity, where it was sprayed with 2 cc of air. Each of the preparations of Formulation Examples 5 and 6 was given as a 20 μl aliquot via a micropipette (*EXCELMYDEGI* 8000, D-5, SANKO JUNYAKU). The preparation of Comparative 1 was given intravenously into a femoral vein of the rat (dose: 1 mg/kg).

After administration of the preparation, blood was taken at a certain interval via a tail vain and examined for the serum concentration of Compound B.

(Results)

Figure 2:
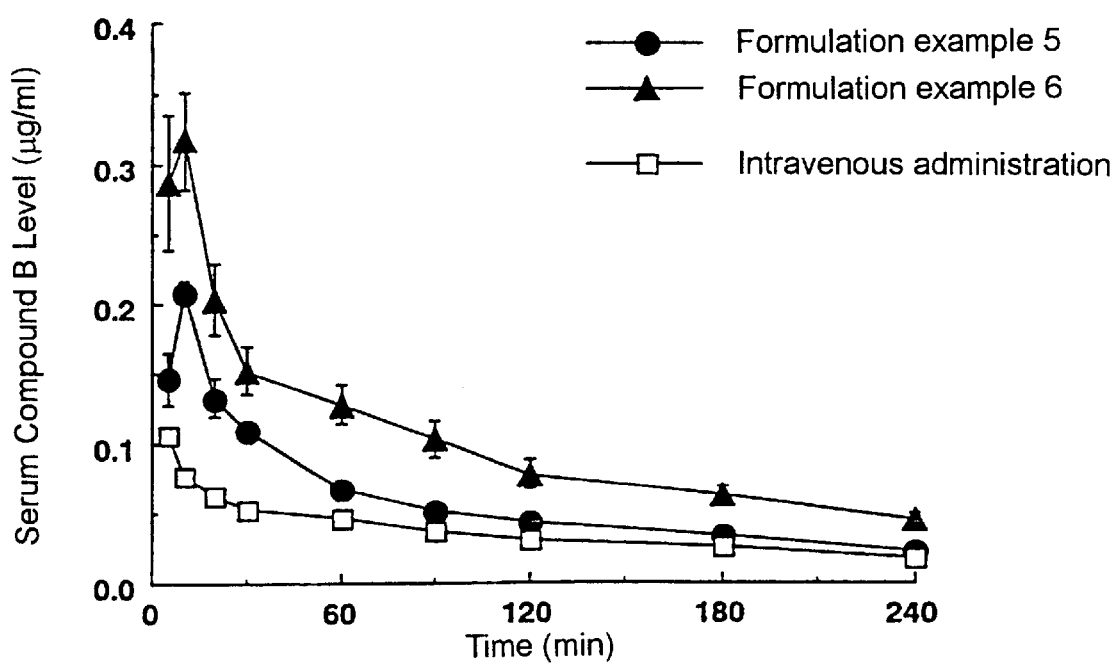
FIG. 2 shows the change in the serum level of Compound B after the nasal administration of Formulations 5 and 6 and after the intravenous administration of the formulation of Comparative 1.

The change in the serum concentration of Compound B is shown in FIG. 1 and FIG. 2. Each preparation of Formulation Examples 1 to 4, 5 and 6 according to the present invention, after given nasally, exhibited the change similar to that observed after an intravenous administration. Accordingly, a nasal administration was proven to enable a rapid in vivo absorption of Compound B.

Experiment 2
(Method)

The efficacy of Compound B was evaluated in a myocardial infarction model employing occlusion and re-perfusion of a rat coronary artery described below.

A male Wistar rat (11 weeks old) was anesthetized with pentobarbital and subjected to a thoracolaparotomy under an artificial respiration. A pericardium was opened to expose the heart, and threaded at the basilar region of the left coronary artery together with the myocardium. About 5.3 mg of the preparation of Formulation Example 3 (1.5 mg/kg as Compound B) was given to the left nasal cavity similarly to Experiment 1. Compound B was dissolved at 2 mg/ml in 0.5% methyl cellulose to obtain a reference control, which was given orally at 5 ml/kg (10 mg/kg as Compound B). The coronary artery was occluded 5 minutes after nasal administration or 1 hour after oral administration. The thread was loosened after 1 hour, and the blood flow was restored and the chest was closed. The animal was returned to the cage as being conscious, and housed until the next day. After 24 hours, the animal was anesthetized again with pentobarbital, received heparin (1000 U/kg) intravenously and then the heart was taken out. The aorta received a retrograde insertion of a polyethylene tube and the heart was made free of any excessive blood using physiological saline. The thread remaining in the myocardium was ligated again and 1% Evans blue was perfused to stain a normal region, whereby determining the ischemic region. Subsequently, the left ventricle was divided into 6 equal portions in parallel with the vertical axis, which were exposed to 1% triphenyltetrazolium chloride at 37° C. for 10 minutes to stain non-necrosis cell, whereby weighing an infarction focus.
(Results)

Each infarction focus was represented as % by weight per ischemic region. The results of Formulation Example 3 or a reference control were represented also by % based on % by weight of the infarction focus per ischemic region after nasal administration only of calcium carbonate or after oral administration only of 0.5% methyl cellulose being regarded as 100. It is evident that the nasal preparation exhibited a high myocardial infarction focus reducing effect when compared with the oral administration in spite of a lower dose.

TABLE 1

|  | Infarction weight/ischemic region (%) | (%) |
|---|---|---|
| Calcium carbonate | 55.3 | 100 |
| Formulation Example 3 | 31.4 | 56.8 |
| 0.5% Methyl cellulose | 60.3 | 100 |
| Reference control | 41.1 | 68.2 |

INDUSTRIAL APPLICABILITY

Since the nasal preparation according to the present invention exhibits an excellent in vivo absorption performance and has an Na—H exchange inhibitory activity which is more excellent than that of an oral preparation, it is useful as a prophylactic and therapeutic agent against an ischemic heart disease such as myocardial infarction and arrhythmia.

What is claimed is:

1. (S)-(−)-7-(5-Fluoro-2-methylphenyl)-5-guanidinoimino-4-methyl-5,6,7,8-tetrahydroquinoline or a prodrug or a salt thereof.

2. (S)-(−)-7-(2-Chloro-5-fluorophenyl)-5-guanidinoimino-4-methyl-5,6,7,8-tetrahydroquinoline or a prodrug or a salt thereof.

3. A composition comprising (S)-(−)-7-(5-fluoro-2-methylphenyl)-5-guanidinoimino-4-methyl-5,6,7,8-tetrahydroquinoline or a prodrug or a salt thereof; or (S)-(−)-7-(2-chloro-5-fluorophenyl)-5-guanidinoimino-4-methyl-5,6,7,8-tetrahydroquinoline or a prodrug or a salt thereof and a pharmaceutically acceptable carrier.

4. A method for inhibiting Na—H exchange in mammals comprising administering an effective amount of (S)-(−)-7-(5-fluoro-2-methylphenyl)-5-guanidinoimino-4-methyl-5,6,7,8-tetrahydroquinoline or a prodrug or a salt thereof; or (S)-(−)-7-(2-chloro-5-fluorophenyl)-5-guanidinoimino-4-methyl-5,6,7,8-tetrahydroquinoline or a prodrug or a salt thereof to said mammals.

* * * * *

UNITED STATES PATENT AND TRADEMARK OFFICE
CERTIFICATE OF CORRECTION

PATENT NO. : 6,706,732 B1
DATED : March 16, 2004
INVENTOR(S) : Masafumi Misaki et al.

Page 1 of 1

It is certified that error appears in the above-identified patent and that said Letters Patent is hereby corrected as shown below:

<u>Title page,</u>
Item [75], Inventors, should read -- Mitsuru Shiraishi, Amagasaki (JP); Shoji Fukumoto, Kobe (JP) --

Signed and Sealed this

Twenty-fifth Day of May, 2004

JON W. DUDAS
*Acting Director of the United States Patent and Trademark Office*